(12) United States Patent
Boye et al.

(10) Patent No.: US 8,298,818 B2
(45) Date of Patent: Oct. 30, 2012

(54) SELF-COMPLEMENTARY ADENO-ASSOCIATED VIRUS HAVING A TRUNCATED CMV-CHICKEN β-ACTIN PROMOTER

(75) Inventors: Sanford Leon Boye, Gainesville, FL (US); William W. Hauswirth, Gainesville, FL (US); Barry John Byrne, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 492 days.

(21) Appl. No.: 12/298,845

(22) PCT Filed: Apr. 27, 2007

(86) PCT No.: PCT/US2007/010338
§ 371 (c)(1),
(2), (4) Date: Dec. 2, 2009

(87) PCT Pub. No.: WO2007/127428
PCT Pub. Date: Nov. 8, 2007

(65) Prior Publication Data
US 2010/0069467 A1     Mar. 18, 2010

Related U.S. Application Data

(60) Provisional application No. 60/795,759, filed on Apr. 28, 2006.

(51) Int. Cl.
*C12N 15/00*     (2006.01)
*C12N 5/00*      (2006.01)

(52) U.S. Cl. ........................... 435/320.1; 435/325

(58) Field of Classification Search ................ 424/93.2; 435/320.1, 325
See application file for complete search history.

(56) References Cited

U.S. PATENT DOCUMENTS

| | | | |
|---|---|---|---|
| 4,683,202 A | 7/1987 | Mullis | |
| 5,013,556 A | 5/1991 | Woodle et al. | |
| 5,043,164 A | 8/1991 | Huang et al. | |
| 5,168,062 A | 12/1992 | Stinski | |
| 5,385,839 A | 1/1995 | Stinski | |
| 5,686,101 A | 11/1997 | Tagawa et al. | |
| 5,705,187 A | 1/1998 | Unger | |
| 5,817,856 A | 10/1998 | Tirosh et al. | |
| 5,820,873 A | 10/1998 | Choi et al. | |
| 5,928,906 A | 7/1999 | Koster et al. | |
| 6,172,188 B1 | 1/2001 | Thastrup et al. | |
| 7,714,119 B2 * | 5/2010 | Fang et al. | 536/23.53 |
| 2004/0022766 A1 | 2/2004 | Acland et al. | |

FOREIGN PATENT DOCUMENTS

| WO | WO 95/07463 | 3/1995 |
|---|---|---|
| WO | WO 01/83692 | 11/2001 |

OTHER PUBLICATIONS

Gong (Brain Res., 2004, vol. 14, No. 1, p. 18-24).*
Gong (Brain Res. Protocols, 2004, vol. 14, p. 18-24.*
McCarty (Gene Therapy, 2003, vol. 10, p. 2112-2118).*
McCarty (Gene Therapy, 2001, vol. 8, p. 1248-1254.*
Mah (Human Gene Therapy, Jan. 20, 2003, vol. 14, p. 143-152).*
Ackland, G. M. et al. "Long-Term Restoration of Rod and Cone Vision by Single Dose rAAV-Mediated Gene Transfer to the Retina in a Canine Model of Childhood Blindness" *Molecular Therapy*, Dec. 2005, pp. 1072-1082, vol. 12, No. 6.
Mah, C. et al. "Dual Vectors Expressing Murine Factor VIII Result in Sustained Correction of Hemophilia A Mice" *Human Gene Therapy*, Jan. 20, 2003, pp. 143-152, vol. 14.
Haire, S. E. et al. "Light-Driven Cone Arrestin Translocation in Cones of Postnatal Guanylate Cyclase-1 Knockout Mouse Retina Treated with AAV-GC1" *Investigative Ophthalmology & Visual Science*, Sep. 2006, pp. 3745-3753, vol. 47, No. 9.
Gao, G. et al. "New Recombinant Serotypes of AAV Vectors" *Current Gene Therapy*, 2005, pp. 285-297, vol. 5.
Warrington, K. H. et al. "Treatment of human disease by adeno-associated viral gene transfer" *Hum. Genet.*, 2006, pp. 571-603, vol. 119.
Snyder, R. O. et al. "Features of the Adeno-Associated Virus Origin Involved in Substrate Recognition by the Viral Rep Protein" *Journal of Virology*, Oct. 1993, pp. 6096-6104, vol. 67, No. 10.
Han, Z. et al. "Down-regulation of expression of rat pyruvate dehydrogenase E1α gene by self-complementary adeno-associated virus-mediated small interfering RNA delivery" *Mitochondrion*, 2007, pp. 253-259, vol. 7.
Wu, J. et al. "Self-Complementary Recombinant Adeno-Associated Viral Vectors: Packaging Capacity and the Role of Rep Proteins in Vector Purity" *Human Gene Therapy*, Feb. 2007, pp. 171-182, vol. 18.
Nathwani, A. C. et al. "Safe and efficient transduction of the liver after peripheral vein infusion of self-complementary AAV vector results in stable therapeutic expression of human FIX in nonhuman primates" *Blood*, Feb. 15, 2007, pp. 1414-1421, vol. 109, No. 4.
Nathwani, A. C. et al. "Self-complementary adeno-associated virus vectors containing a novel liver-specific human factor IX expression cassette enable highly efficient transduction of murine and nonhuman primate liver" *Blood*, Apr. 1, 2006, pp. 2653-2661, vol. 107, No. 7.

(Continued)

*Primary Examiner* — Michael C. Wilson
(74) *Attorney, Agent, or Firm* — Saliwanchik, Lloyd & Eisenschenk

(57) ABSTRACT

The present inventors concerns vectors carrying a truncated chimeric CMV-chicken β-actin (smCBA) promoter in which the hybrid chicken β-actin/rabbit β-globin intron is greatly shortened, and their use to deliver to an operatively linked polynucleotide to host cells in vitro or in vivo, resulting in expression of the polynucleotide in the host cells. In one embodiment, the vector carrying the smCBA promoter is administered to the eye. In another embodiment, the vector carrying the smCBA promoter is a self-complementary adeno-associated virus (AAV). The AAV vector may be of any serotype (e.g., type 1, type 2, type 3, type 4, type 5, type 6, type 7, type 8, type 9, type 10). In another embodiment, a self-complementary vector carrying the smCBA promoter is administered to the eye. Another aspect of the invention concerns host cells carrying a vector of the invention. Another aspect of the invention concerns pharmaceutical composition comprising the vectors or host cells of the invention, and a pharmaceutically acceptable carrier.

11 Claims, 12 Drawing Sheets

OTHER PUBLICATIONS

Choi, V. W. et al. "Effects of Adeno-Associated Virus DNA Hairpin Structure on Recombination" *Journal of Virology*, Jun. 2005, pp. 6801-6807, vol. 79, No. 11.

Zhong, L. et al. "Self-complementary Adeno-associated Virus 2 (AAV)-T Cell Protein Tyrosine Phosphatase Vectors as Helper Viruses to Improve Transduction Efficiency of Conventional Single-Stranded AAV Vectors in Vitro and in Vivo" *Molecular Therapy*, Nov. 2004, pp. 950-957, vol. 10, No. 5.

Fu, H. et al. "Self-Complementary Adeno-associated Virus Serotype 2 Vector: Global Distribution and Broad Dispersion of AAV-Mediated Transgene Expression in Mouse Brain" *Molecular Therapy*, Dec. 2003, pp. 911-917, vol. 8, No. 6.

McCarty, D. M. et al. "Adeno-associated virus terminal repeat (TR) mutant generates self-complementary vectors to overcome the rate-limiting step to transduction in vivo" *Gene Therapy*, 2003, pp. 2112-2118, vol. 10.

McCarty, D. M. et al. "Self-complementary recombinant adeno-associated virus (scAAV) vectors promote efficient transduction independently of DNA synthesis" *Gene Therapy*, 2001, pp. 1248-1254, vol. 8.

Ding, W. et al. "Second-Strand Genome Conversion of Adeno-Associated Virus type 2 (AAV-2) and AAV-5 is Not Rate Limiting following Apical Infection of Polarized Human Airway Epithelia" *Journal of Virology*, Jul. 2003, pp. 7361-7366, vol. 77, No. 13.

Chalfie, M. et al. "Green Fluorescent Protein as a Marker for Gene Expression" *Science*, Feb. 11, 1994, pp. 802-805, vol. 263.

Prasher, D. C. "Using GFP to see the light" *Trends in Genetics*, 1995, pp. 320-323, vol. 11, No. 8.

Heim, R. et al. "Wavelength mutations and posttranslational autoxidation of green fluorescent protein" *Proc. Natl. Acad. Sci. USA*, Dec. 1994, pp. 12501-12504, vol. 91.

Miller, M. D. et al. "The Active Site of *Serratia* Endonuclease Contains a Conserved Magnesium-Water Cluster" *J. Mol. Biol.*, 1999, pp. 975-987, vol. 288.

Weiss, T. S. et al. "Gαi3 binding to calnuc on Golgi membranes in living cells monitored by fluorescence resonance energy transfer of green fluorescent protein fusion proteins" *PNAS*, Dec. 18, 2001, pp. 14961-14966, vol. 98, No. 26.

Majoul, I. et al. "KDEL-Cargo Regulates Interactions between Proteins Involved in COPI Vesicle Traffic Measurements in Living Cells Using FRET" *Developmental Cell*, Jul. 2001, pp. 139-153, vol. 1.

Laird, D. W. et al. "Comparative Analysis and Application of Fluorescent Protein-Tagged Connexins" *Microscopy Research and Technique*, 2001, pp. 263-272, vol. 52.

Dabrowski, S. et al. "Use of the Green Fluorescent Protein Variant (YFP) to Monitor MetArg Human Proinsulin Production in *Escherichia coli*" *Protein Expression and Purification*, 1999, pp. 315-323, vol. 16.

Fradkov, A. F. et al. "Novel fluorescent protein from *Discosoma* coral and its mutants possesses a unique far-red fluorescence" *FEBS Letters*, 2000, pp. 127-130, vol. 479.

Templeton, N. S. et al. "Improved DNA: liposome complexes for increased systemic delivery and gene expression" *Nature Biotechnology*, Jul. 1997, pp. 647-652, vol. 15.

Ho, R. J. Y. et al. "Target-sensitive Immunoliposomes as an Efficient Drug Carrier for Antiviral Activity" *The Journal of Biological Chemistry*, Oct. 15, 1987, pp. 13973-13978, vol. 262, No. 29.

Ho, R. J. Y. et al. "Interaction of Target-sensitive Immunoliposomes with Herpes Simplex Virus" *The Journal of Biological Chemistry*, Oct. 15, 1997, pp. 13979-13964, vol. 262, No. 29.

Allen, T. M. et al. "Large unilamellar liposomes with low uptake into the reticuloendothelial system" *FEBS Lett.*, Oct. 1987, pp. 42-46, vol. 223, No. 1.

Klibanov, A. L. et al. "Amphipathic polyethyleneglycols effectively prolong the circulation time of liposomes" *FEBS Lett.*, Jul. 1990, pp. 235-237, vol. 268, No. 1.

Russell, D. W. et al. "Human gene targeting by viral vectors" *Nature Genetics*, Apr. 1998, pp. 325-330, vol. 18.

Kachi, S. et al. "Sustained expression after nonviral ocular gene transfer using mammalian promoters" *Gene Therapy*, 2006, pp. 798-804, vol. 13.

Flannery, J. G. et al. "Efficient photoreceptor-targeted gene expression in vivo by recombinant adeno-associated virus" *Proc. Natl. Acad. Sci. USA*, Jun. 1997, pp. 6916-6921, vol. 94.

\* cited by examiner

AAV construct with smCBA driving green fluorescent protein (GFP)

AAV construct with smCBA driving bovine Guanylate Cyclase (bGC1)

AAV construct with smCBA driving mouse beta subunit of phosphodiesterase(β-PDE)

FIG. 5C-1
FIG. 5C-2
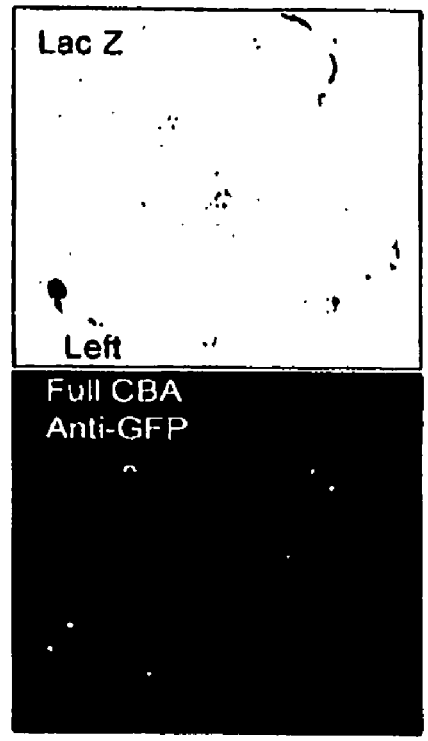
FIG. 5D-1
FIG. 5D-2

SEQUENCE LISTING

<160> NUMBER OF SEQ ID NOS: 1

<210> SEQ ID NO 1
<211> LENGTH: 953
<212> TYPE: DNA
<213> ORGANISM: Artificial Sequence
<220> FEATURE:
<223> OTHER INFORMATION: truncated chimeric CMV-chicken beta-actin
      (smCBA) promoter

<400> SEQUENCE: 1

```
aattcggtac cctagttatt aatagtaatc aattacgggg tcattagttc atagcccata        60
tatggagttc cgcgttacat aacttacggt aaatggcccg cctggctgac cgcccaacga       120
cccccgccca ttgacgtcaa taatgacgta tgttcccata gtaacgccaa tagggacttt       180
ccattgacgt caatgggtgg actatttacg gtaaactgcc cacttggcag tacatcaagt       240
gtatcatatg ccaagtacgc ccctattga cgtcaatgac ggtaaatggc ccgcctggca       300
ttatgcccag tacatgacct tatgggactt tcctacttgg cagtacatct acgtattagt       360
catcgctatt accatggtcg aggtgagccc cacgttctgc ttcactctcc ccatctcccc       420
cccctcccca ccccaatttt gtatttatt tattttttaa ttattttgtg cagcgatggg       480
```

```
ggcgggggg   ggggggggc   gcgcgccagg   cggggcgggg   cggggcgagg   ggcggggcgg    540
ggcgaggcgg  agaggtgcgg  cggcagccaa   tcagagcggc   gcgctccgaa   agtttcctttt   600 tatggcgagg  cggcggcggc  ggcggcccta   taaaaagcga   agcgcgcggc   gggcgggagt    660
cgctgcgacg  ctgccttcgc  cccgtgcccc   gctccgccgc   cgcctcgcgc   cgcccgcccc   720
ggctctgact  gaccgcgtta  ctcccacagg   tgagcgggcg   ggacggccct   tctcctccgg    780
gctgtaatta  gcgcttggtt  taatgacggc   ttgtttctttt  tctgtggctg   cgtgaaagcc    840
ttgaggggct  ccgggagcta  gagcctctgc   taaccatgtt   catgccttct   tcttttttcct    900 acagctcctg  ggcaacgtgc  tggttattgt   gctgtctcat   cattttggca   aag           953
```

SELF-COMPLEMENTARY ADENO-ASSOCIATED VIRUS HAVING A TRUNCATED CMV-CHICKEN β-ACTIN PROMOTER

CROSS-REFERENCE TO RELATED APPLICATION

The present application is the National Stage of International Application No. PCT/US2007/010338, filed Apr. 27, 2007, which claims the benefit of U.S. Provisional Application Ser. No. 60/795,759, filed Apr. 28, 2006, which is hereby incorporated by reference herein in its entirety, including any figures, tables, nucleic acid sequences, amino acid sequences, and drawings.

BACKGROUND OF THE INVENTION

Recombinant adeno-associated virus (rAAV) has widely been used as a vehicle for the delivery of genetic material to target cells. AAV has several advantages over other viral vectors. For example, wild-type AAV has not been associated with any pathological human condition, rAAV does not contain native viral coding sequence and persistent expression of delivered transgenes has been observed in many applications.

Under normal circumstances, AAV packages a single-stranded DNA molecule of up to 4800 nucleotides in length. Following infection of cells by the virus, the intrinsic molecular machinery of the cell is required for conversion of single-stranded DNA into double stranded form. The double-stranded form is then capable of being transcribed, thereby allowing expression of the delivered gene to commence. It has been shown in a number of cell and tissue types that second strand synthesis of DNA by the host cell is the rate-limiting step in expression. By virtue of already being packaged as a double stranded DNA molecule, self-complementary AAV (scAAV) bypasses this step, thereby greatly reducing the time to onset of gene expression.

Self-complementary AAV is generated through the use of vector plasmid with a mutation in one of the terminal resolution sequences of the AAV virus. This mutation leads to the packaging of a self-complementary, double-stranded DNA molecule covalently linked at one end. Vector genomes are required to be approximately half genome size (2.4 KB) in order to package effectively in the normal AAV capsid. Because of this size limitation, large promoters are unsuitable for use with scAAV. Most broad applications to date have used the cytomegalovirus immediate early promoter (CMV) alone for driving transgene expression. However, it has been shown by others that transgene expression with CMV markedly drops off in certain tissue types, such as eye and liver, sometimes as early as two weeks post-injection. A long acting, ubiquitous promoter of small size would be very useful in a scAAV system.

The chimeric CMV-chicken β-actin promoter (CBA) has been utilized extensively as a promoter that supports expression in a wide variety of cells when in rAAV vectors delivered to retina. In addition to broad tropism, the present inventors have observed that CBA also has the capacity to promote expression for long periods post infection (Acland, G. M. et al. *Mol. Ther.*, 2005, 12(6):1072-1082). CBA is ~1700 base pairs in length, too large in most cases to be used in conjunction with scAAV to deliver cDNAs (over 300 bps pairs in length).

BRIEF SUMMARY OF THE INVENTION

The present invention concerns vectors carrying a truncated chimeric CMV-chicken β-actin (smCBA) promoter in which the hybrid chicken β-actin/rabbit β-globin intron is greatly shortened, and their use to deliver to host cells in vitro or in vivo a polynucleotide operatively linked to the truncated promoter, resulting in expression of the polynucleotide in the host cells. Use of the smCBA promoter has several advantages: (1) the promoter can be used with various serotypes of adeno-associated virus (AAV); (2) expression of the polynucleotide (e.g., transgene) is initiated sooner than with other promoters; (3) expression of the polynucleotide is maintained for a longer period of time, compared to expression using other promoters; and (4) because the promoter is truncated, it permits packaging of more polynucleotide(s) into the vector, which is particularly relevant for double-stranded viral vectors.

In one embodiment, the vector carrying the smCBA promoter is administered to the eye. In another embodiment, the vector carrying the smCBA promoter is a self-complementary AAV. The AAV vector may be of any serotype (e.g., type 1, type 2, type 3, type 4, type 5, type 6, type 7, type 8, type 9, type 10). In another embodiment, a self-complementary vector carrying the smCBA promoter is administered to the eye. Another aspect of the invention concerns host cells carrying a vector of the invention. Another aspect of the invention concerns a pharmaceutical composition comprising the vectors or host cells of the invention and a pharmaceutically acceptable carrier.

BRIEF DESCRIPTION OF THE DRAWINGS

FIG. 4A shows an AAV construct of the invention with smCBA driving green fluorescent protein (GFP) expression. FIG. 4B shows an AAV construct of the invention with smCBA driving expression of bovine Guanaylate Cyclase (bGC1). FIG. 4C shows an AAV construction of the invention with smCBA driving mouse beta subunit of phosphodiesterase β-PDE).

FIGS. 5A-1, 5A-2, 5B-1, 5B-2, 5C-1, 5C-2, 5D-1, and 5D-2 show neonate C57Black6 mice subretinally injected with AAV2-smCBA-GFP or AAV2-CBA-GFP with equal amounts (1:1) AAV2-CMV-LacZ. Whole mount retinas stained for LacZ and anti-GFP.

FIGS. 6A-1, 6A-2, 6B-1, and 6B-2 show adult C57Black6 mouse subretinally injected with AAV2-smCBA-GFP (left eye) or AAV2-CBA-GFP (right eye) with equal amount (1:1) AAV2-CMV-LacZ. Whole mount retina stained for LacZ and anti-GFP.

DETAILED DESCRIPTION OF THE INVENTION

The present inventors have made a truncated chimeric cytomegalovirus (CMV)-chicken β-actin (CBA) promoter (smCBA) in which the hybrid chicken β-actin/rabbit β-globin intron is greatly shortened (Mah C. et al. *Hum. Gene Ther.*, 2003, 14(2):143-152). Full CBA was first cut with the restriction endonuclease Bsp 120I and treated with exonuclease to polish the end, subsequently the DNA was cut with Xba I and treated with DNA polymerase to fill the restricted end. A ligation of the blunt ends resulted in the formation of smCBA. The total size of smCBA is 953 bps versus 1714 bps for full length CBA.

The smCBA promoter is described in Mah, C. et al., *Hum. Gene Ther.*, 2003, 14(2):143-152 and Haire, S. E. et al. *Invest. Opthalmol. Vis. Sci.*, 2006, 47(9):3745-3753, which are each incorporated herein by reference in its entirety. The nucleic acid sequence of the smCBA promoter is:

```
                                        (SEQ ID NO: 1)
aattcggtaccctagttattaatagtaatcaattacggggtcattagttc atagcccatatatggagttccgcgttacataacttacggtaaatggcccg cctggctgaccgcccaacgaccccgcccattgacgtcaataatgacgta tgttcccatagtaacgccaatagggactttccattgacgtcaatgggtgg actatttacggtaaactgcccacttggcagtacatcaagtgtatcatatg ccaagtacgccccctattgacgtcaatgacggtaaatggcccgcctggca ttatgcccagtacatgaccttatgggactttcctacttggcagtacatct acgtattagtcatcgctattaccatggtcgaggtgagccccacgttctgc ttcactctccccatctccccccctccccacccccaattttgtatttatt tattttttaattattttgtgcagcgatgggggcggggggggggggggggc gcgcgccaggcggggcggggcgggcgaggggcggggcggggcgaggcgg agaggtgcggcggcagccaatcagagcggcgcgctccgaaagtttcctt
```

-continued
```
tatggcgaggcggcggcggcggcggcccctataaaaagcgaagcgcgcggc gggcgggagtcgctgcgacgctgccttcgccccgtgccccgctccgccgc cgcctcgcgccgcccgccccggctctgactgaccgcgttactcccacagg tgagcgggcgggacggcccttctcctccgggctgtaattagcgcttggtt taatgacggcttgtttcttttctgtggctgcgtgaaagccttgagggct ccgggagctagagcctctgctaaccatgttcatgccttcttcttttcct acagctcctgggcaacgtgctggttattgtgctgtctcatcattttggca aag.
```

Experiments evaluating tropism (cell type targeting) and extent and duration of transgene expression by smCBA relative to full CBA in mouse retina resulted in the two promoters being interchangeable. As such, the present inventors have created a scAAV construct with smCBA driving expression of humanized green fluorescent protein (GFP) and analyzed the progression of gene expression relative to the matched standard AAV construct with full length CBA (CBA-GFP). These comparisons have been done with AAV packaged in capsid serotypes 1, 2 and 5. The present inventors have also evaluated transgene expression when virus is delivered to the vitreous, as well as subretinally.

Figure 1:
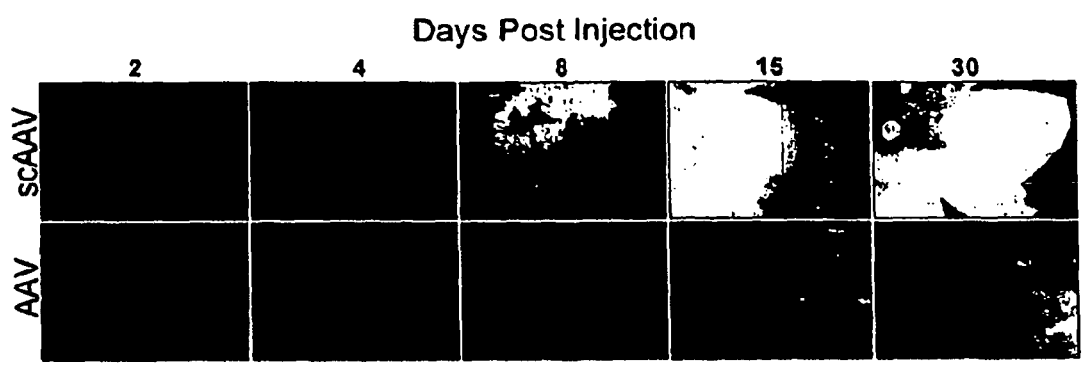
FIG. 1 shows images of whole mount mouse retina after single subretinal injection of type 2 self complimentary AAV (scAAV) or type 2 standard AAV expressing green fluorescent protein under the control of smCBA.

Results with serotype 2 in mouse retina indicate onset of transgene expression is markedly faster with scAAV2-smCBA-GFP than with the corresponding AAV2-CBA-GFP (see FIG. 1). Typically, expression of GFP with AAV2-CBA-GFP is first apparent at 15 days post-injection whereas expression from scAAV-smCBA-GFP was seen as early as two days post-injection, with robust expression at day 8.

Figure 2:
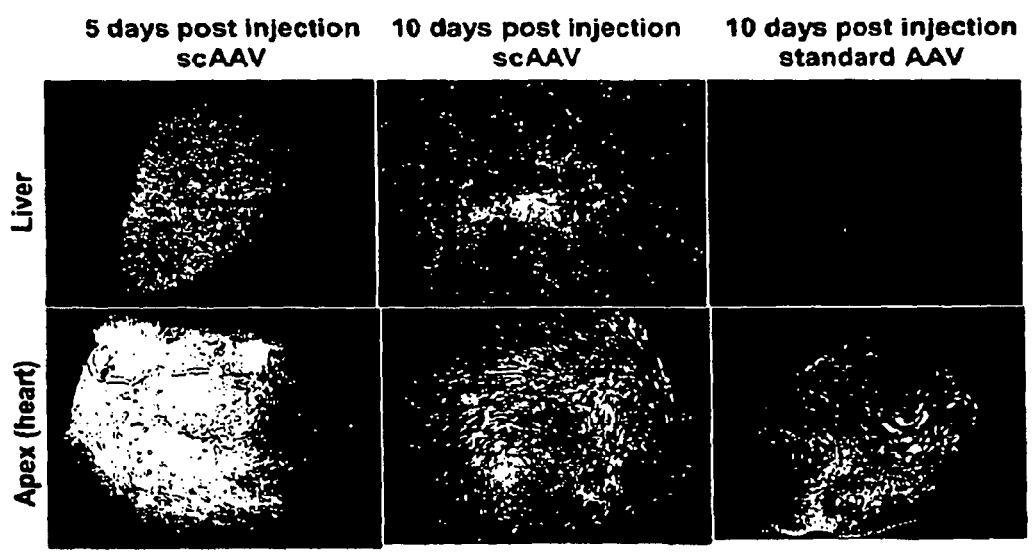
FIG. 2 shows transduction of heart and liver following para-cardial or intra-cardial injection (respectively) of type I scAAV-sm CBA-GFP or standard AAV-CBA-GFP.

Results of scAAV1-smCBA-GFP (serotype I) injected into the paracardial space of mice indicate efficient expression of GFP in myocytes 5 days post-injection. In addition, efficient transduction of liver was achieved by intracardial injection of the same (type I) virus at day 5 post-injection (see FIG. 2). Standard AAV1-CBA-GFP controls for both heart and liver were negative at 10 days post injection.

Self-complementary AAV has been established as a faster system of transgene expression than standard AAV, yet it retains the same advantages of AAV over other gene delivery viral vectors. The broad tropism and small size of the smCBA coupled to scAAV create a gene delivery system that can target a number of tissue types faster than the current conventional AAV constructs. In addition, smCBA supports persistent expression, and given its smaller size can accommodate larger gene constructs in the scAAV system. In the Examples, the smCBA promoter is compared to the CMV promoter (U.S. Pat. Nos. 5,168,062 and 5,385,839, which are each incorporated herein by reference in their entirety).

The present invention concerns vectors carrying a truncated chimeric CMV-chicken β-actin (smCBA) promoter in which the hybrid chicken β-actin/rabbit β-globin intron is greatly shortened, and their use to deliver to an operatively linked polynucleotide to host cells in vitro or in vivo, resulting in expression of the polynucleotide in the host cells. Preferably, the vector carrying the smCBA promoter is a self-complementary adeno-associated virus (AAV); however, other viral or non-viral vectors such as lentivirus or liposomes can be utilized.

The vector carrying the smCBA promoter can be administered to any anatomical site on or in the subject. In one embodiment, the vector carrying the smCBA promoter is administered to the eye. For example, the vector can be administered to the eye by subretinal or intravitreal injection.

In another embodiment, a self-complementary AAV vector carrying the smCBA promoter is administered to the eye. Examples of polynucleotides and vectors useful for treating ocular disorders, and methods for their administration, are described in U.S. patent publication 20040022766 (Acland, G. M. et al.), filed Nov. 20, 2002, and Acland G. M. et al., *Molecular Therapy*, 2005 Dec., 12(6):1072-1082, which are each incorporated herein by reference in its entirety. The smCBA promoter can be placed in a vector described in the aforementioned publications. The smCBA promoter can be operably-linked with a polynucleotide described in the aforementioned publications. The smCBA promoter can be placed in a vector and be operably-linked to a polynucleotide to treat an ocular disorder described in the aforementioned publications.

In those embodiments in which an AAV vector (e.g., a self-complementary AAV vector) is utilized to carry the smCBA promoter, the AAV vector may be of any serotype (e.g., type 1, type 2, type 3, type 4, type 5, type 6, type 7, type 8, type 9, type 10, or others). Examples of AAV serotypes that may be utilized in the present invention include, but are not limited to, those described in Gao G. et al., *Curr. Gene Ther.*, 2005, 5(3):285-297, which is incorporated herein by reference in its entirety.

One aspect of the invention provides a method for delivering a polynucleotide to a host cell in vitro or in vivo, comprising administering a vector containing the polynucleotide operably-linked to a smCBA promoter to the host cell, wherein the polynucleotide is expressed in the host cell. The polynucleotide may be one that is found naturally within the host cell and/or encodes a polypeptide that is found naturally within the host cell (i.e., that is endogenous to the host cell). Alternatively, the polynucleotide may be one that is not found naturally in the host cell and/or encodes a polypeptide that is not found naturally in the host cell (i.e., is heterologous to the host cell).

According to the in vivo methods of the present invention, a vector containing a polynucleotide operably-linked to a smCBA promoter can be administered to a human or non-human subject. The vector may be administered, for example, in order to alleviate (e.g., reduce or eliminate) one or more symptoms associated with a pathologic disorder. Treatment with the vector is intended to include prophylactic intervention to prevent or reduce onset of the symptoms associated with the disorder. The vectors, host cells, and pharmaceutical compositions containing them can be co-administered (concurrently or consecutively) to a subject with other therapeutic agents, for example. Examples of pathologic disorders that may be treated using the vectors of the invention, and corresponding therapeutic polynucleotides useful for treating the disorders, include (but are not limited to) those described in Warrington, K. H. and Herzog, R. W. *Hum. Genet.*, 2006 Apr. 13, Epub ahead of print, and Mah, C. et al. *Human Gene Therapy*, 2003, 14:143-152, which are each incorporated herein by reference in its entirety. The vectors, host cells, and compositions of the invention can be administered to the subject systemically (e.g., orally, intravenously) or locally at a target anatomical site.

The methods of the invention may include further steps in addition to administration of the vector, host cell, or pharmaceutical composition. In some embodiments, a subject with the disorder is identified or a subject at risk for the disorder is identified. A subject may be someone who has not been diagnosed with the disease or condition (diagnosis, prognosis, and/or staging) or someone diagnosed with the disease or condition (diagnosis, prognosis, monitoring, and/or staging), including someone treated for the disease or condition (prognosis, staging, and/or monitoring). Optionally, diagnosis can include identifying a subject suffering from or at risk for developing the disorder. Alternatively, the subject may not have been diagnosed with the disorder but suspected of having the disorder based either on patient history or family history, or the exhibition or observation of characteristic symptoms, for example.

Optionally, the methods of the invention can include a step of analyzing expression of the polynucleotide delivered in vitro or in vivo to the host cells. The step of analyzing the expression of a polynucleotide can be performed in a variety of different ways. Numerous suitable techniques are known for analyzing protein expression. For example, protein expression can be determined directly by assessing protein expression of cells or fluid of a biological sample. Protein expression can be detected using immunological techniques, e.g., using antibodies that specifically bind the protein (e.g., a therapeutic protein) in assays such as immunofluorescence or immunohistochemical staining and analysis, enzyme-linked immunosorbent assay (ELISA), radioimmunoassay (RIA), immunoblotting (e.g., Western blotting), and like techniques. Expression of a polynucleotide can also be determined by directly or indirectly measuring the amount of mRNA encoded by the polynucleotide in a cellular sample using known techniques such as Northern blotting and PCR-based methods such as competitive quantitative reverse transcriptase PCR (Q-RT-PCR).

Vectors

Any of a variety of nucleic acid vectors may be used to deliver and express a polynucleotide operatively linked to the truncated chimeric CMV-chicken β-actin promoter in accordance with the methods of the invention, e.g., recombinant viruses, such as recombinant adeno-associated virus (AAV), lentivirus, recombinant adenoviruses, recombinant retroviruses, recombinant poxviruses, recombinant baculovirus, and other viruses known in the art, as well as plasmids, cosmids and phages, etc. A wealth of publications known to those of skill in the art discusses the use of a variety of such vectors for delivery of genes (see, e.g., Ausubel et al., Current Protocols in Molecular Biology, John Wiley & Sons, New York, 1989; Kay, M. A. et al, 2001 *Nat. Medic.*, 7(1):33-40; and Walther W. and Stein U., Drugs, 2000, 60(2):249-7.1, which are each incorporated herein by reference in their entirety).

In one embodiment, the recombinant AAV vector is a self-complementary AAV. In one embodiment of the invention, the vector is a recombinant self-complementary AAV carrying a wild-type normal) version of a selected transgene-encoding cDNA driven by a truncated chimeric CMV-chicken β-actin promoter that expresses the product of the wild-type cDNA in selected ocular cells of the affected subject. To exemplify the methods and compositions of this invention, the presently preferred vector, a recombinant AAV is described in detail.

Adeno-associated viruses are small, single-stranded DNA viruses which require helper virus to facilitate efficient replication (K. I. Berns, Parvoviridae: the viruses and their replication, p. 1007-1041, in F. N. Fields et al., Fundamental Virology, 3rd ed., vol. 2, (Lippencott-Raven Publishers, Philadelphia, Pa.) (1995)). The 4.7 kb genome of AAV is characterized by two inverted terminal repeats (ITR) and two open reading frames which encode the Rep proteins and Cap proteins, respectively. The Rep reading frame encodes four proteins of molecular weight 78 kD, 68 kD, 52 kD and 40 kD. These proteins function mainly in regulating AAV replication and rescue and integration of the AAV into a host cell's chromosomes. The Cap reading frame encodes three structural proteins of molecular weight 85 kD (VP1), 72 kD (VP2)

and 61 kD (VP3) which form the virion capsid. More than 80% of total proteins in AAV virion comprise VP3.

Flanking the rep and cap open reading frames at the 5' and 3' ends are 145 by inverted terminal repeats (ITRs), the first 125 by of which are capable of forming Y- or T-shaped duplex structures. The two ITRs are the only cis elements essential for AAV replication, rescue, packaging and integration of the AAV genome. There are two conformations of AAV ITRs called "flip" and "flop". These differences in conformation originated from the replication model of adeno-associated virus which uses the ITR to initiate and reinitiate the replication (R. O. Snyder et al., 1993, *J Virol.*, 67:6096-6104 (1993); K. I. Berns, 1990 *Microbiological Reviews,* 54:316-329, which are incorporated herein by reference in their entirety). The entire rep and cap domains can be excised and replaced with a therapeutic or reporter transgene (B. J. Carter, in "Handbook of Parvoviruses", ed., P. Tijsser, CRC Press, pp. 155-168 (1990)).

AAVs have been found in many animal species, including primates, canine, fowl and human (F. A. Murphy et al., "The Classification and Nomenclature of Viruses: Sixth Report of the International Committee on Taxonomy of Viruses", Archives of Virology, (Springer-Verlag, Vienna) (1995)). Several primate serotypes have been reported (e.g., AAV1, AAV2, AAV3, AAV4, AAV5 and AAV6). The AAV ITR sequences and other AAV sequences employed in constructs used in the present invention may be obtained from a variety of sources. For example, the sequences may be provided by AAV type 5, AAV type 2, AAV type 1, AAV type 3, AAV type 4, AAV type 6, or other AAV serotypes or other densoviruses, including presently identified human AAV types and AAV serotypes yet to be identified. Similarly, AAVs known to infect other animals may also provide these ITRs employed in the molecules or constructs of this invention. Similarly; the capsids from a variety of serotypes of AAV may be "mixed and matched" with the other vector components. See, e.g., International Patent Publication No. WO 01/83692, published Nov. 8, 2001, which is incorporated herein by reference in its entirety. A variety of these viral serotypes and strains are available from the American Type Culture Collection, Manassas, Va., or are available from a variety of academic or commercial sources. Alternatively, it may be desirable to synthesize sequences used in preparing the vectors and viruses of the invention using known techniques, which may utilize AAV sequences that are published and/or available from a variety of databases. The source of the sequences utilized in preparation of the constructs of the invention, is not a limitation of the present invention. Similarly, the selection of the species and serotype of AAV that provides these sequences is within the skill of the artisan and does not limit the following invention.

Examples of self-complementary AAV vectors that may be used in the vectors, host cells, and methods of the invention are described, for example, in Han Z. et al., *Mitochondrion,* 2007, Feb. 20, Epub ahead of print; Wu J. et al., *Hum Gene Ther.,* 2007, 18(2):171-182; Nathwani A. C. et al., *Blood,* 2007, 109(4):1414-1421; Nathwani A. C. et al., *Blood,* 2006, 107(7):2653-2661, Epub 2005 Dec. 1; Choi V. W. et al, *J. Virol.,* 2005, 79(11):6801-6807; Xu D. et al., 2005, 11(4): 523-530; Zhong L. et al., *Mol. Ther.,* 2004, 10(5):950-957; Fu H. et al., *Mol. Ther.,* 2003, 8(6):911-917; McCarty D. M. et al., *Gene Ther.,* 2003, 10(26):2112-2118; Ding W. et al., *J. Virol.,* 77(13):7361-7366; and McCarty D. M. et al., *Gene Ther.,* 2001, 8(16):1248-1254, which are each incorporated herein by reference in its entirety.

Host Cells

Examples of target cells to which the vectors of the present invention can be administered in vitro or in vivo include, but are not limited to, those listed in Table 1. As will be understood by one of skill in the art, there are over 200 cell types in the human body. It is believed that the methods of the subject invention can be used to deliver polynucleotides to any of these cell types for therapeutic or other purposes. For example, any cell arising from the ectoderm, mesoderm, or endoderm germ cell layers can be a target cell for administration of the vectors of the invention. In one embodiment, the host cell is a liver cell. In another embodiment, the host cell is a non-liver cell. In another embodiment, the host cells are ocular cells, such as cells of the retina (e.g., retinal pigment epithelial cells). In another embodiment, the host cells are muscle cells. In another embodiment, the host cells are heart cells.

The terms "recombinant host cells", "host cells", "genetically modified host cells" "cells", "cell lines", "cell cultures", and other such terms denoting microorganisms or higher eukaryotic cells refer to cells that can be, or have been, used as recipients for recombinant vectors or other transfer DNA, immaterial of the method by which the DNA is introduced into the cell or the subsequent disposition of the cell. The terms include the progeny of the original cell that has been transfected. Cells in primary culture can also be used as recipients. Host cells can range in plasticity and proliferation potential.

Host cells can be differentiated cells, progenitor cells, or stem cells, for example. Thus, the cells can range in plasticity from totipotent or pluripotent stem cells (e.g., adult or embryonic), precursor or progenitor cells, to highly specialized cells, such as those of the central nervous system (e.g., neurons and glia). Stem cells can be obtained from a variety of sources, including embryonic tissue, fetal tissue, adult tissue, umbilical cord blood, peripheral blood, bone marrow, and brain, for example.

Host cells can be genetically modified with the vectors of the present invention. The vector may be in the form of a plasmid, a virus, (e.g., AAV, lentivirus, or other virus), a viral particle, a phage, etc. The genetically modified host cells can be cultured in conventional nutrient media modified as appropriate for activating promoters, selecting transformants/transfectants or amplifying the subunit-encoding polynucleotide. The culture conditions, such as temperature, pH and the like, generally are similar to those previously used with the host cell selected for expression, and will be apparent to those of skill in the art.

In one embodiment, the host cell is a human cell. In another embodiment, the host cell is a non-human animal cell. In another embodiment, the host cell is a vertebrate cell. In another embodiment, the host cell is a mammalian cell. It will be understood by one of skill in the art that the methods of the present invention are also applicable for veterinary purposes. For example, host cells of non-human animals can find application either in human or animal patients (e.g., veterinary uses).

Both prokaryotic and eukaryotic host cells may be used for expression of desired coding sequences when appropriate control sequences (e.g., promoter sequences) that are compatible with the designated host are used. For example, among prokaryotic hosts, *Escherichia coli* may be used. Transfer vectors compatible with prokaryotic hosts can be derived from, for example, the plasmid pBR322 that contains operons conferring ampicillin and tetracycline resistance, and the various pUC vectors, that also contain sequences conferring antibiotic resistance markers. These markers may be used to obtain successful transformants by selection. Eukaryotic hosts include yeast and mammalian cells in culture systems. *Pichia pastoris, Saccharomyces cerevisiae* and *S. carlsbergensis* are commonly used yeast hosts. Yeast-compatible vectors carry markers that permit selection of successful transformants by conferring protrophy to auxotrophic mutants or resistance to heavy metals on wild-type strains. Yeast compatible vectors may employ the 2-µ origin of replication (Broach et al. *Meth. Enzymol.* 101:307, 1983), the combination of CEN3 and ARS1 or other means for assuring replication, such as sequences that will result in incorporation of an appropriate fragment into the host cell genome.

The invention encompasses the host cells transformed by a vector according to the invention. These cells may be obtained by introducing (in vitro or in vivo) into host cells a nucleotide sequence inserted into a vector as defined above. Optionally, if the cells are isolated, the cells can be cultured under conditions allowing the replication and/or the expression of the polynucleotide sequences carried by the vector.

Host cells useful for expression of the polynucleotides may be primary cells or cells of cell lines. The host cells may be tumor cells or non-tumor cells. Mammalian cell lines available as hosts for expression are known in the art and are available from depositories such as the American Type Culture Collection. These include but are not limited to HeLa cells, human embryonic kidney (HEK) cells, Chinese hamster ovary (CHO) cells, baby hamster kidney (BHK) cells, and others.

Reporter Polypeptides

The polynucleotide carried by the vector of the present invention can encode a reporter polypeptide (also referred to herein interchangeably as the "reporter gene" or "marker gene"). The polynucleotide encoding the reporter polypeptide may be the only transgene carried by the vector; alternatively, other polynucleotides may be present in addition to the reporter gene such as those encoding useful polypeptides (e.g., therapeutic polypeptides) or useful inhibitory nucleic acids (such as antisense oligonucleotides or interfering RNA. Reporter polypeptides such as Beta-globin, CAT, luciferase, and beta-gal may be used. Preferably, the reporter polypeptide is one whose production can be detected (and, optionally, measured qualitatively, quantitatively, and/or semi-quantitatively) in living, intact cells. Examples of such reporter polypeptides include fluorescent polypeptides (also referred to herein as fluorescent proteins (FP)) such as the green fluorescent proteins (GFP), and variants of GFP such as yellow fluorescent proteins (YFP), etc., for example, PS-FP (Yang F. et al., *Nat. Biotechno.*, 1996, 10:1246-1251; Cubitt A. B. et al., "Understanding Structure-Function Relationships in the *Aequorea victoria* Green Fluorescent Protein, in Methods in Cell Biology, Vol. 58, Green Fluorescent Protein, Academic Press, 1999:19-29; Kain S. R., "Enhanced Variants of the Green Fluorescent Protein for Greater Sensitivity, Different Colours and Detection of Apoptosis", in Fluorescent and Luminescent Probes, $2^{nd}$ Edition, 1999, Chapter 19:284-292; Tsien R. Y., *Annu. Rev. Biochem.*, 1998, 67:509-544; Eisenstein, M., *Nature Methods*, January 2005, Research Highlights, 2(1):8-9; each of which are incorporated herein by reference in their entirety). As used herein, "variants of GFP" include, but are not limited to, polypeptides known in the art as green fluorescent protein-like proteins, GFP-like chromoproteins, green fluorescent protein fragments, red fluorescent proteins, and orange fluorescent proteins.

In addition, the vector of the present invention may optionally include another marker gene such as an antibiotic resistance gene and the fluorescent protein is used here as a visualization marker gene for example, FP/PS1/Ble, to aid visualization and fluorescent quantitation of the protein. Many FPs, originally isolated from the jellyfish *Aequorea Victoria* (for example, GFP) retain their fluorescent properties when expressed in heterologous cells, thereby providing a powerful tool as fluorescent recombinant probes to monitor cellular events or functions (see, for example, Chalfie et al., *Science*, 1994, 263(5148):802-805; Prasher, *Trends Genet.*, 1995, 11(8):320-3; and PCT publication no. WO 95/07463, each of which are incorporated herein by reference in their entirety).

Several spectral and mutational variants of GFP proteins have since been isolated, for example, the naturally occurring blue-fluorescent variant of GFP (Heim et al., *Proc. Natl. Acad. Sci. USA*, 1994, 91(26):12501-4; U.S. Pat. No. 6,172,188, both of which are incorporated herein by reference), the yellow-fluorescent protein variant of GFP (Miller et al., *J. Mol. Biol.*, 1999, 288:975-987; Weiss, et al., *Proc. Natl. Acad. Sci. USA*, 2001, 98(26):14961-62001; Majoul, et al., *Dev. Cell.*, 2001, 1(1):139-53; Laird et al., *Microsc. Res. Tech.*, 2001; 52(3):263-72; Daabrowski et al. *Protein Expr. Purif.*, 1999, 16(2):315-23, and more recently the red fluorescent protein isolated from the coral Discosoma (Fradkov et al., *FEBS Lett.*, 2000, 479(3):127-30; Miller et al., *J. Mol. Biol.*, 1999, 288:975-987), which allows the use of fluorescent probes having different excitation and emission spectra permitting the simultaneous monitoring of more than one process. GFP proteins provide non-invasive assays that allow detection of cellular events in intact, living cells. The skilled artisan will recognize that the invention is not limited to the fluorescent polypeptides explicitly described herein and one may use any other spectral or mutational variant or derivative in accordance with the present invention.

Several methods to identify and quantitate cells that are fluorescently tagged with fluorescent gene products are well known in the art and may be used in the context of the present invention. One example is the use of fluorescent activated cell sorting (FACS); flow cytometry or flow microfluorometry provides the means of scanning individual cells for the presence of a fluorescent protein. The method employs instrumentation that is capable of activating, and detecting the excitation emissions of cells that express a fluorescent marker in a liquid medium. FACS is unique in its ability to provide a rapid, reliable, quantitative, and multi-parameter analysis on either living or fixed cells in culture or in vivo. Other methods to measure fluorescent markers are also well known.

Formulations and Therapeutic/Prophylactic Administration Thereof

Mammalian species which benefit from the disclosed methods of polynucleotide delivery include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. The terms "patient" and "subject" are used interchangeably herein are intended to include such human and non-human mammalian species. According to the in vivo methods of the present invention, an effective amount of a viral or non-viral vector carrying a polynucleotide operatively linked to the smCBA promoter is administered to cells of a subject, wherein the polynucleotide is then expressed in the cells. The polynucleotide may encode a polypeptide that is naturally occurring within the subject's species or a different mammalian species. The expression vectors used in the subject invention can comprise nucleic acid sequences encoding any human or non-human mammalian polypeptide. In instances where host cells carrying the vectors of the invention are administered to a subject, the cells may be autogenic, allogeneic, or xenogeneic, for example.

The pharmaceutical compositions of the present invention can be formulated according to known methods for preparing pharmaceutically useful compositions. Furthermore, as used herein, the phrase "pharmaceutically acceptable carrier" includes any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations containing pharmaceutically acceptable carriers are described in a number of sources which are well known and readily available to those skilled in the art. For example, *Remington's Pharmaceutical Sciences* (Martin E. W., 1995, Easton Pa., Mack Publishing Company, 19$^{th}$ ed.), which is incorporated herein by reference in its entirety, describes formulations that can be used in connection with the subject invention.

Pharmaceutical compositions of the present invention useful for parenteral injection can include pharmaceutically acceptable sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents, or vehicles include water, ethanol, polyols (such as glycerol, propylene glycol, polyethylene, lycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. Formulations suitable for parenteral administration include, for example, aqueous injectable solutions that may contain antioxidants, buffers, and solutes which render the formulation isotonic with the blood of the intended recipient; and aqueous and nonaqueous sterile suspensions, which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that, in addition to the ingredients particularly mentioned above, the formulations of the subject invention can include other agents conventional in the art having regard to the type of formulation in question.

The pharmaceutical compositions used in the methods of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption, such as aluminum monostearate and gelatin.

In some cases, in order to prolong the effect of the active agent (e.g., a polypeptide encoded by the polynucleotide to be administered), it is desirable to slow the absorption from subcutaneous or intramuscular injection. This may be accomplished by the use of a liquid suspension of crystalline or amorphous material with poor water solubility.

Injectable depot forms are made by forming microencapsule matrices of the agent (e.g., vectors or host cells of the invention) in biodegradable polymers such as polylactide-polyglycolide. Depending upon the ratio of active agent (e.g., polynucleotide or encoded polypeptide) to polymer and the nature of the particular polymer employed, the rate of release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active agents (e.g., vectors or host cells of the invention) are mixed with it least one pharmaceutically acceptable excipient or carrier such as sodium nitrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, capsules, pills, and granules can be prepared with coatings and shells such as enteric coatings and other coatings well known in the pharmaceutical formulating art. Optionally, the solid dosage forms contain opacifying agents, and can be of a composition that releases the vector or host cells at a target anatomical site. Examples of embedding compositions that can be used include polymeric substances and waxes. The active agents (e.g., vectors or host cells of the invention) can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the vectors or host cells of the invention, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung, eye, etc. Compositions for topical administration, including those for inhalation, may be prepared as a dry powder, which may be pressurized or non-pressurized. In non-pressurized powder compositions, the active ingredients in finely divided form may be used in admixture with a larger-sized pharmaceutically acceptable inert carrier comprising particles having a size, for example, of up to 100 µm in diameter. Suitable inert carriers include sugars such as lactose. Desirably, at least 95% by weight of the particles of the active ingredient have an effective particle size in the range of 0.01 to 10 µm.

The pharmaceutical composition of the present invention can include a liposome component. According to the present invention, a liposome comprises a lipid composition that is capable of fusing with the plasma membrane of a cell, thereby allowing the liposome to deliver a construct of the invention into the cell. Some preferred liposomes include those liposomes commonly used in gene delivery methods known to those of skill in the art. Some preferred liposome delivery vehicles comprise multilamellar vesicle (MLV) lipids and extruded lipids, although the invention is not limited to such liposomes. Methods for preparation of MLVs are well known in the art. "Extruded lipids" are also contemplated. Extruded lipids are lipids that are prepared similarly to MLV lipids, but which are subsequently extruded through filters of decreasing size, as described in Templeton et al., *Nature Biotech.*, 1997, 15:647-652, which is incorporated herein by reference in its entirety. Small unilamellar vesicle (SUV) lipids can also be used in the compositions and methods of the present invention. Other preferred liposome delivery vehicles comprise liposomes having a polycationic lipid composition (i.e., cationic liposomes). For example, cationic liposome compositions include, but are not limited to, any cationic liposome complexed with cholesterol, and without limitation, include DOTMA and cholesterol, DOTAP and cholesterol, DOTIM and cholesterol, and DDAB and cholesterol. Liposomes utilized in the present invention can be any size, including from about 10 to 1000 nanometers (nm), or any size in between.

A liposome delivery vehicle can be modified to target a particular site in a mammal, thereby targeting and making use of a polynucleotide carried by a vector of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In one embodiment, other targeting mechanisms, such as targeting by addition of exogenous targeting molecules to a liposome (i.e., antibodies) may not be a necessary component of the liposome of the present invention, since effective immune activation at immunologically active organs can already be provided by the composition when the route of delivery is intravenous or intraperitoneal, without the aid of additional targeting mechanisms. However, in some embodiments, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry*, 1986, 25: 5500-6; Ho et al., *J Biol Chem*, 1987a, 262: 13979-84; Ho et al., *J Biol Chem*, 1987b, 262: 13973-8; and U.S. Pat. No. 4,957,735 to Huang et al., each of which is incorporated herein by reference in its entirety). In one embodiment, if avoidance of the efficient uptake of injected liposomes by reticuloendothelial system cells due to opsonization of liposomes by plasma proteins or other factors is desired, hydrophilic lipids, such as gangliosides (Allen et al., *FEBS Lett*, 1987, 223: 42-6) or polyethylene glycol (PEG)-derived lipids (Klibanov et al., *FEBS Lett*, 1990, 268: 235-7), can be incorporated into the bilayer of a conventional liposome to form the so-called sterically-stabilized or "stealth" liposomes (Woodle et al., *Biochim Biophys Acta*, 1992, 1113: 171-99). Variations of such liposomes are described, for example, in U.S. Pat. No. 5,705,187 to Unger et al., U.S. Pat. No. 5,820,873 to Choi et al., U.S. Pat. No. 5,817,856 to Tirosh et al.; U.S. Pat. No. 5,686,101 to Tagawa et al.; U.S. Pat. No. 5,043,164 to Huang et al., and U.S. Pat. No. 5,013,556 to Woodle et al., all of which are incorporated herein by reference in their entireties).

The methods of this invention, generally speaking, may be practiced using any mode of administration that is medically acceptable, meaning any mode that produces effective levels of response without causing clinically unacceptable adverse effects. Preferred modes of administration include parenteral, injection, infusion, deposition, implantation, anal or vaginal supposition, oral ingestion, inhalation, and topical administration. Injections can be intravenous, intradermal, subcutaneous, intramuscular, or intraperitoneal. For example, the pharmaceutical composition comprising the vectors or host cells of the invention can be injected or topically applied directly into or on to a target anatomical site. In some embodiments, the doses can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially fused pellets. Inhalation includes administering the pharmaceutical composition with an aerosol in an inhaler, either alone or attached to a carrier that can be absorbed. For systemic administration, it may be preferred that the pharmaceutical composition is encapsulated in liposomes. The term "parenteral" includes subcutaneous injections, intravenous, intramuscular, intraperitoneal, intrasternal injection or infusion techniques. In certain preferred embodiments of the invention, the administration can be designed so as to result in sequential exposure of the pharmaceutical composition over some period of time, e.g., hours, days, weeks, months or years. This can be accomplished by repeated administrations of the pharmaceutical composition, by one of the methods described above, or alternatively, by a sustained-release delivery system in which the pharmaceutical composition is delivered to the subject. for a prolonged period without repeated administrations. By sustained-release delivery system, it is meant that total release of the pharmaceutical composition does not occur immediately upon administration, but rather is delayed for some period of time. Release can occur in bursts or it can occur gradually and continuously. Administration of such a system can be, e.g., by long-lasting oral dosage forms, bolus injections, transdermal patches, and subcutaneous implants.

The vectors and host cells of the invention can be incorporated in a physiologically acceptable carrier or salt, suitable for topical application to the affected area, or for direct injection into the affected areas, or for diffusion from an implanted device, for example. Topical applications include use of gels, creams, lotions, suppositories, and use of devices and dressings such as dissolving patches and bandages impregnated with the vectors or host cells of the invention prior to use. Additional routes of delivery include oral, and injection or infusion that is intramuscular, intravenous, subcutaneous, intraperitoneal, intraspinal, and epidural.

DEFINITIONS

As used herein, the term "viral vector" and equivalent terms refer to viruses that are utilized for transferring selected DNA or RNA sequences into a host cell. The vectors may be utilized for the purpose of transferring nucleic acids into cells either in vitro or in vivo. Viruses that have been commonly used for the transfer of genetic material in vivo include the retroviruses, adenoviruses (AV), adeno-associated viruses (AAV), lentiviruses, parvoviruses, and herpes viruses.

As used herein, the term "expression vector", "construct", "expression cassette", and comparable terms refer to a vector that is capable of inducing the expression of nucleic acids that have been cloned into it after transformation into a host cell. Expression cassettes can be placed in viral vectors (e.g., self-complementary AAV vectors, lentiviral vectors) and non-viral vectors (e.g., plasmids, liposomes). The cloned genetic material is usually placed under the control of (i.e., operably linked to) certain regulatory sequences such a promoters or enhancers. Promoter sequences may be constitutive, inducible, or repressible. Any prokaryotic or eukaryotic cell that is the recipient of a vector is the host for that vector. The term encompasses prokaryotic or eukaryotic cells that have been engineered to incorporate a gene in their genome. Cells that can serve as hosts are well known in the art as are techniques for cellular transformation (see e.g., Sambrook, et al., Molecular Cloning: A Laboratory Manual, 2nd ed., Cold Spring Harbor (1989)).

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. The phrases "operable linked", "operatively positioned", "operatively linked", "under control", and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence. The vectors of the invention utilize a truncated chimeric CMV-chicken β-actin (smCBA) promoter operatively linked to a polynucleotide of interest.

A promoter may be one naturally associated with a gene or sequence, as may be obtained by isolating the 5' non-coding sequences located upstream of the coding segment and/or exon. Such a promoter can be referred to as "endogenous". Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

As used herein, the terms "substantially pure" or "purified" mean that the desired product (e.g., polynucleotide) is essentially free from contaminating cellular components. Containments may include, but are not limited to, proteins, carbohydrates and lipids. One method for determining the purity of a protein or nucleic acid is by electrophoresis in a matrix such as polyacrylamide or agarose. Purity is evidence by the appearance of a single band after staining.

As indicated above, a nucleic acid sequence that initiates the transcription of a gene is a promoter. Promoters are typically found 5' to the gene and located proximal to the start codon. If a promotor is of the inducible type, then the rate of transcription increases in response to an inducing agent. Expression is the process by which a polypeptide is produced from a nucleic acid sequence. The process involves the transcription of the gene or coding sequence into mRNA and the translation of this mRNA into a polypeptide. Depending on the context in which it is used, the term "expression" may refer to the production of RNA, protein, or both.

As used herein, the term "recombinant" refers to nucleic acid that is formed by combining nucleic acid sequences and sequence elements. A recombinant host is any host receiving a recombinant nucleic acid and the term "recombinant protein" refers to protein produced by such a host.

As used herein, the term "polynucleotide" (e.g., polynucleotide encoding a polypeptide) can include a nucleic acid sequence encoding a polypeptide and additional nucleic acid sequences that are coding or non-coding sequences. The term "polynucleotide" is inclusive of the terms "gene", "transgene", and "coding sequence", for example. The term "polynucleotide" can include nucleic acid sequences useful in the constructs of the present invention. For example, a regulatory component that may be used in the vectors of the invention is an internal ribosome entry site (IRES). An IRES sequence, or other suitable systems may be used to produce more than one gene product (e.g., polypeptide) from a single gene transcript. An IRES (or other suitable sequence) is used to produce a polypeptide that contains more than one polypeptide chain (e.g., a fusion protein or multimer) or to express two different proteins from or within the same cell. An exemplary IRES is the poliovirus internal ribosome entry sequence, which supports transgene expression in photoreceptors, RPE and ganglion cells. Preferably, the IRES is located 3' to the transgene in the rAAV vector. In one embodiment, an IRES element is used to produce a reporter polypeptide such as GFP.

As used herein, the terms "gene", "transgene", and "coding sequence" refer to the nucleic acid sequence that undergoes transcription as the result of promoter activity. A gene may code for a particular polypeptide or for an RNA sequence that is of interest in itself, e.g. because it acts as an antisense oligonucleotide or interfering RNA. The gene(s) carried by the vector of the invention can encode any substance that is desired to be delivered to a cell, including, without limitation, a polypeptide, protein, enzyme, carbohydrate, chemical moiety, or nucleic acid sequences which may include oligonucleotides, RNA, and/or DNA. Typically, a gene carried by a vector of the invention refers to a nucleic acid sequence heterologous to the vector, encoding a desired product, e.g., a polypeptide or RNA of interest, and the regulatory sequences which direct transcription and/or translation thereof in a host cell, and permit expression of the encoded product in a host cell. In one embodiment, the gene may be a nucleic acid molecule that introduces specific genetic modifications into human chromosomes, e.g., for correction of mutated genes. See, e.g., D. W. Russell & R. K. Hirata, 1998, *Nat. Genet.*, 18:325-330, which is incorporated herein by reference in its entirety.

Polynucleotides carried by the vectors of the invention may encode polypeptides or other molecules (e.g., interfering RNA) useful in treating a disorder, such as enzymes, cytokines, hormones, structural proteins, antigens to induce an immunogenic response, etc. The term "treating" or "treatment" as used herein encompasses both prophylactic and therapeutic treatment. Treatment includes alleviation of one or more symptoms of the disorder and may correct the disorder. Prophylaxis includes delaying onset of the disorder (e.g., delaying onset of an infection) and may include prevention of the disorder.

The terms "operatively linked" and "operably linked" are used interchangeably herein to refer to the functional relationship between a promoter sequence (e.g., a truncated chimeric CMV-chicken β-actin promoter) and a polynucleotide, such that the promoter sequence drives expression of the polynucleotide.

The term "protein", "polypeptide", and "peptide" are used herein interchangeably to refer to an amino acid sequence of any length. The polypeptide encoded by the polynucleotide carried by the vector of the invention may be a multimeric construct (e.g., a fusion protein). Multimeric constructs of the subject invention typically comprise a series of repeating elements, optionally interspersed with other elements. As would be appreciated by one skilled in the art, the order in which the repeating elements occur in the multimeric polypeptide is not critical and any arrangement of the repeating elements as set forth herein can be provided by the subject invention. Thus, a "multimeric construct" according to the subject invention can provide a multimeric polypeptide comprising a series of polypeptides, polypeptide fragments, or epitopes that are, optionally, joined together by linker elements (either chemical linker elements or amino acid linker elements).

The terms "cell" and "cells" are used interchangeably herein to refer to a single cell or plurality of cells (i.e., at least one cell). Host cells can be isolated or present in a subject in vivo.

Methods involving conventional molecular biology techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990. Methods for chemical synthesis of nucleic acids are discussed, for example, in Beaucage and Carruthers, *Tetra Letts.*, 1981, 22:1859-1862, and Matteucci et al., *J. Am. Chem. Soc.*, 1981, 103:3185. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Following are examples that illustrate materials, methods, and procedures for practicing the invention. The examples are illustrative and should not be construed as limiting.

EXAMPLE 1

Transduction and Tropism of an Abbreviated Form of CMV-Chicken β-Actin Promoter (CBA) with AAV in Mouse Retina The chimeric CMV-chicken β-actin promoter (CBA) has been utilized extensively as a promoter of expression in a wide variety of cell types when delivered by recombinant adeno-associated virus (rAAV) vectors. Besides broad tropism, CBA has the capacity to promote expression for long periods post-infection, in our experience up to 5 years in retina (Acland et al., *Mol. Ther.*, 2005, 12(6):1072-1082, which is incorporated herein by reference in its entirety). Another commonly used broad tropism promoter, cytomegalovirus immediate early promoter (CMV), while much smaller in size, has shown a tendency to 'shutdown' in relatively quick fashion (Kachi et al., *Gene Ther.*, 2006, 13(9): 798-804, which is incorporated herein by reference in its entirety). Because of the restrictive packaging capacity of AAV (4.8 kb), the large size of CBA (1.7 kb) greatly limits the size of a cDNA that can expressed in a rAAV construct. The development of self-complementary AAV vectors with even less packaging capacity than standard AAV has further highlighted the utility of a smaller version of CBA that still retains broad tropism and sustained expression.

A. CBA vs. smCBA Comparison

Figure 3:
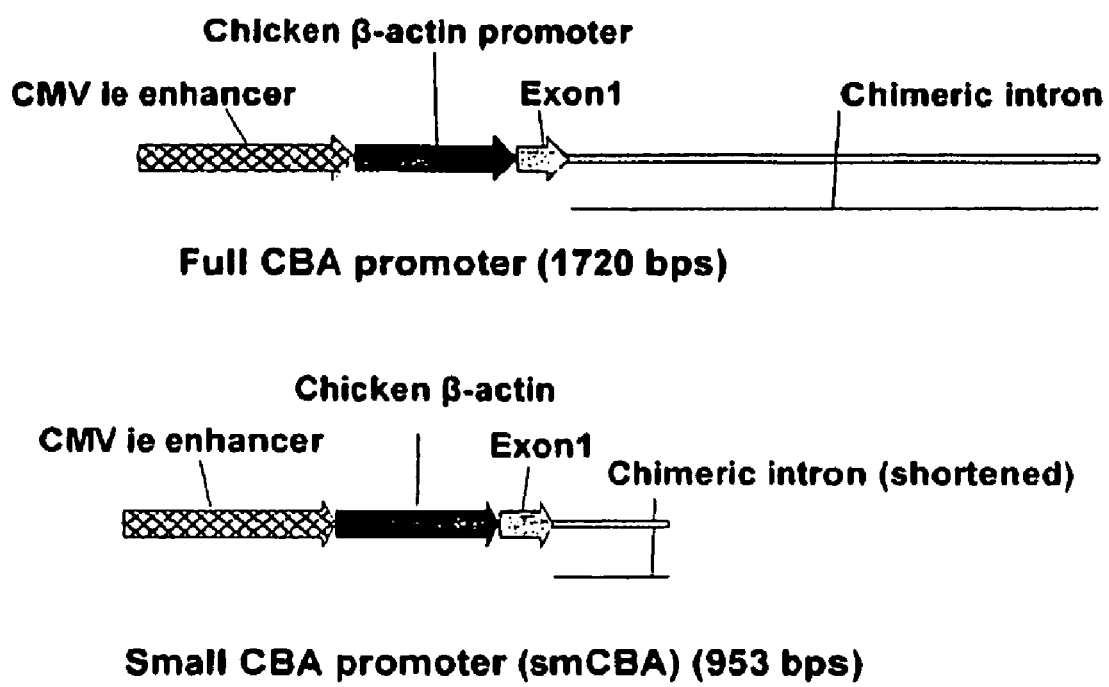
FIG. 3 shows versions of the chimeric CMV-chicken β-actin promoter (CBA).
Figure 4A:
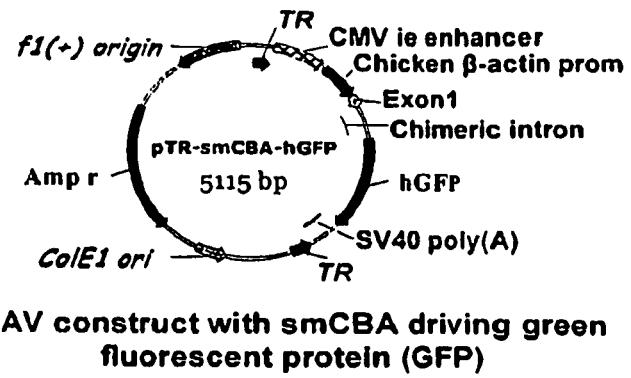
FIGS. 4A-4C show smCBA AAV constructs.
Figure 4B:
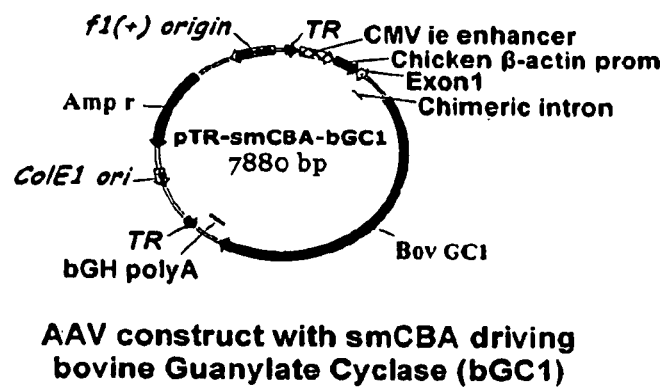
Figure 4C:
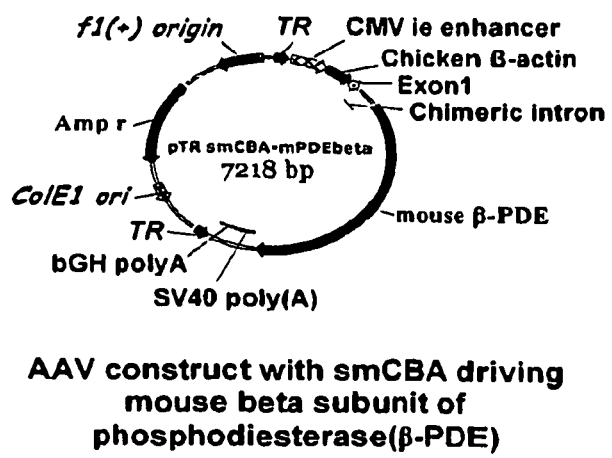
Figures 1, 5A:
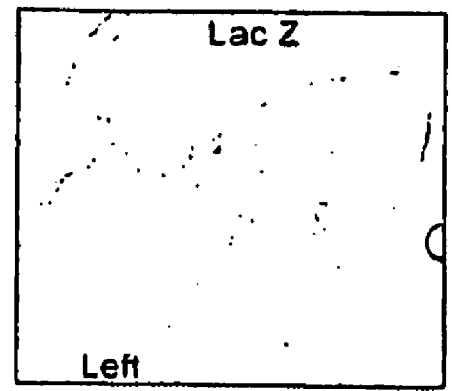
Figures 2, 5A:
Figures 1, 5B:
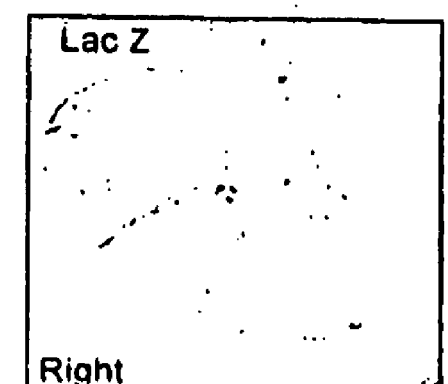
Figures 2, 5B:
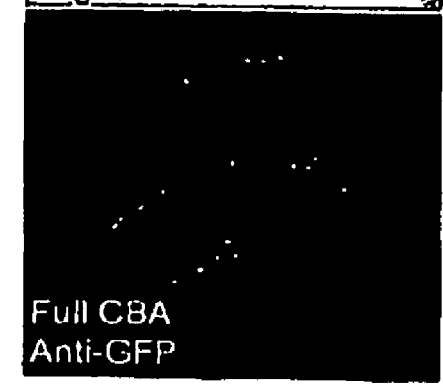
Figures 1, 6A:
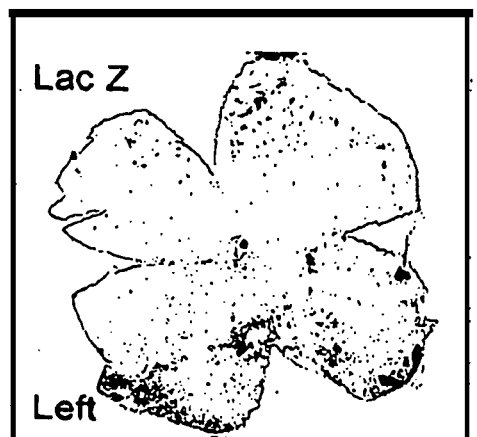
Figures 2, 6A:
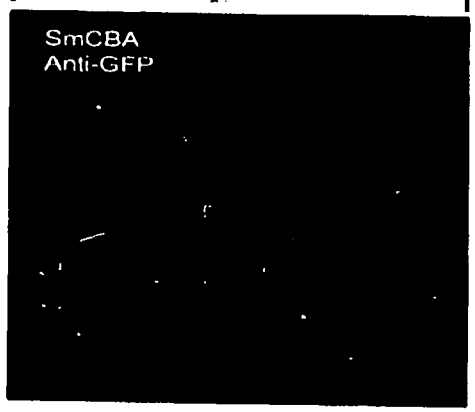
Figures 1, 6B:
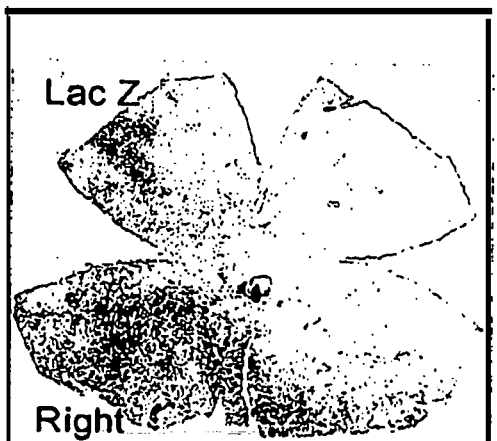
Figures 2, 6B:
Figure 7:
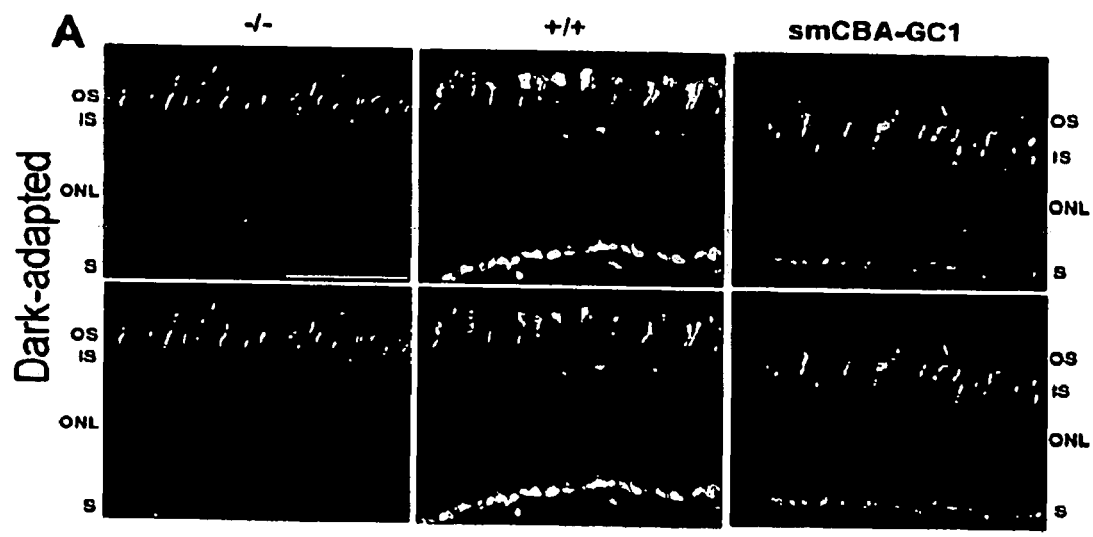
FIG. 7 shows immunolocalization of GC1 (red) and cone arrestin (green) in age matched Guanylate cyclase (GC1) knockout (left), wild type (middle) and AAV5-smCBA-GC1-treated GC1 KO mouse (right) retinas. Images taken at 8 weeks of age.
Figure 8:
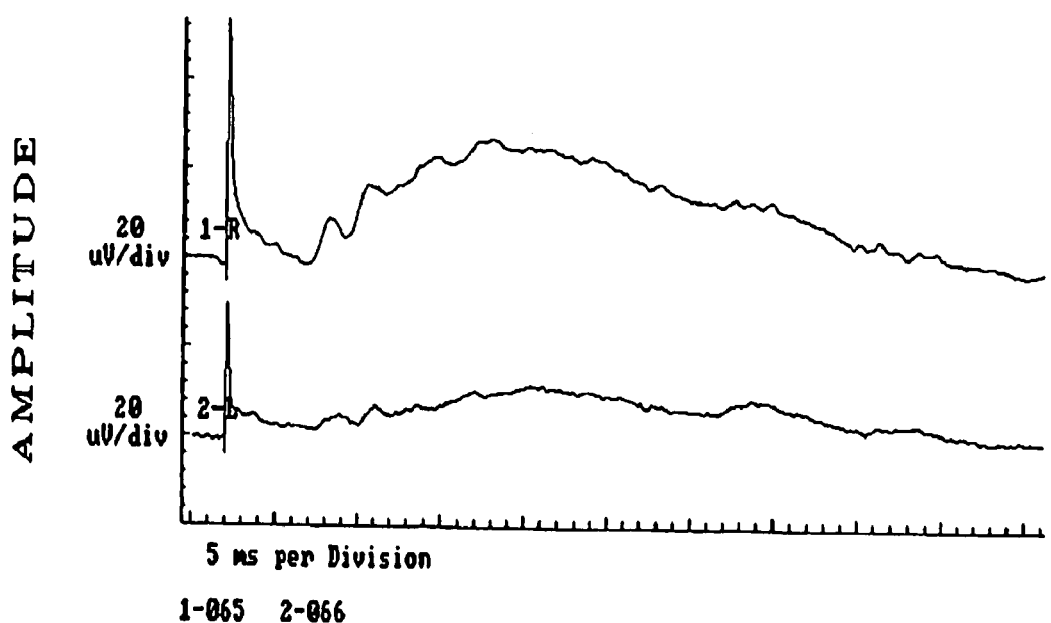
FIG. 8 shows full-field scotopic flash ERG responses at 10 cds/m2 recorded from injected (R) and uninjected (L) eyes of an rd10 mouse 3 weeks post-subretinal injection with AAV5-smCBA-mPDEbeta.
Figure 9:
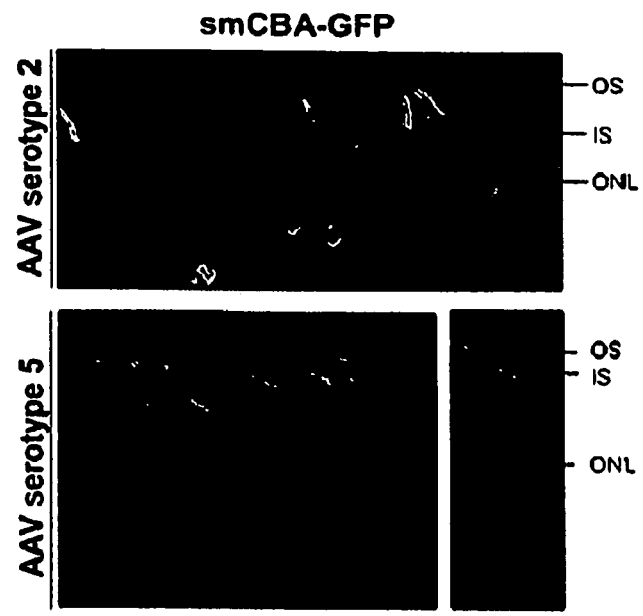
FIG. 9 shows representative sections of AAV-smCBA-GFP serotype 2 and 5 at 5 weeks post-injection in C57Black6 mice, stained with DAPI and anti-GFP.
Figure 10:
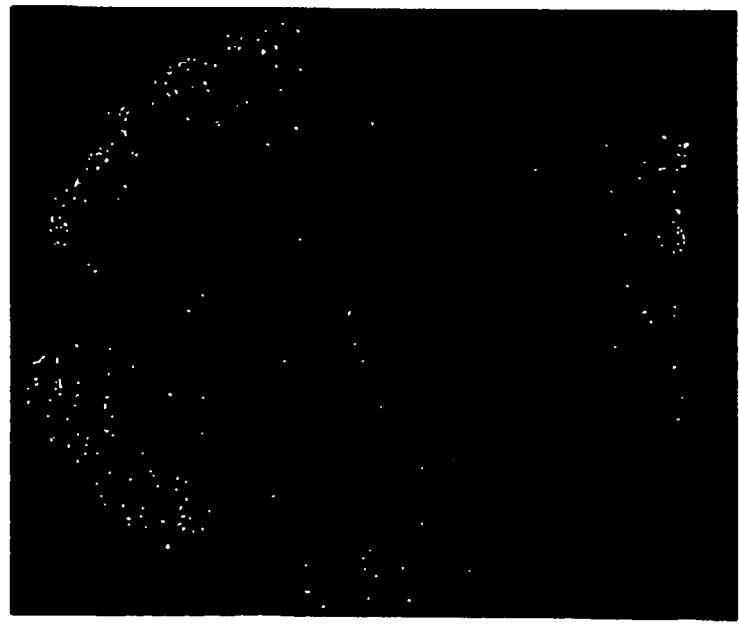
FIG. 10 shows adult C57Black6 mouse 7 months post-subretinal injection with AAV2-smCBA-GFP, Whole mount retina stained for anti-GFP.

The present inventors directly compared the expression pattern of full-length CBA (1720 bases) to a smaller version, smCBA (953 bases), in which the hybrid chicken β-actin/rabbit β-globin intron is greatly shortened (shown in FIG. 3). Neonate and adult C57Black6 mice were injected subretinally with $1\times10^{10}$ vg/ml of AAV serotype 2 containing smCBA driving green fluorescent protein (AAV2-smCBA-GFP) or the same construct with the full CBA promoter (AAV2-CBA-GFP). Each injection contained an equal amount of AAV2-CMV-LacZ as internal standard, thereby accounting for injection variation. Whole mount retinas were examined 3-4 weeks post injection by both LacZ staining and anti-GFP antibody staining. SmCBA AAV constructs are shown in FIGS. 4A-4C. Results are shown in FIGS. 5-10.

B. Long-Term Persistence of smCBA Driven Expression and Evaluation of Rescue in Retinal Degenerative Animal Models AAV-smCBA constructs driving transgene expression were evaluated for rescue in two separate retinal degenerative mouse models, the RD10 mutant and the GC1 knock-out. Control injections of AAV2-smCBA-GFP or AAV5-smCBA-GFP vectors were used to evaluate persistence of smCBA expression. Rescue was determined using ERG analysis for the RD10 model and restoration of protein translocation (as measured by immunohistochemistry) in the Gc1 knock-out. GFP and transgene expression was evaluated up to 6 months post-injection.

C. Cell Specificity/Targeting of smCBA

Injected eyecups were enucleated, sectioned and immunostained with antibodies against GFP. Sections were counterstained with DAPI and visualized with fluorescent and confocal microscopy.

D. Conclusions

Results of AAV mediated transgene expression following subretinal delivery to mouse retina indicate that the smCBA promoter is equivalent to the full-length CBA promoter. smCBA allows the incorporation of larger cDNAs into AAV vectors. Recent advances with self-complementary AAV (scAAV) vectors highlight the need for small promoters capable of driving sustained transgene expression that exhibit broad tropism, such as smCBA.

EXAMPLE 2

Self-Complementary AAV Vectors Promote Fast and Efficient Transduction of Mouse Retina Adeno-associated virus packages a single-stranded DNA molecule of up to 4800 nucleotides in length. Following infection of cells by virus, intrinsic molecular machinery of the cell is required for conversion of single stranded DNA into double stranded form. This second strand synthesis is the rate limiting step to transduction by AAV. Recently, self-complementary (double-stranded) adeno-associated virus (scAAV) has been shown to promote faster transduction than matched standard AAV in selected mouse tissues (McCarty et al., *Gene Ther.*, 2003, Dec. 10(26):2112-2118, which is incorporated herein by reference in its entirety). The goal in these experiments was to compare the temporal and cell-type transduction properties of scAAV vectors when delivered to the mouse retina to those already established for standard AAV vectors.

A. AAV Vectors

Figure 11B:
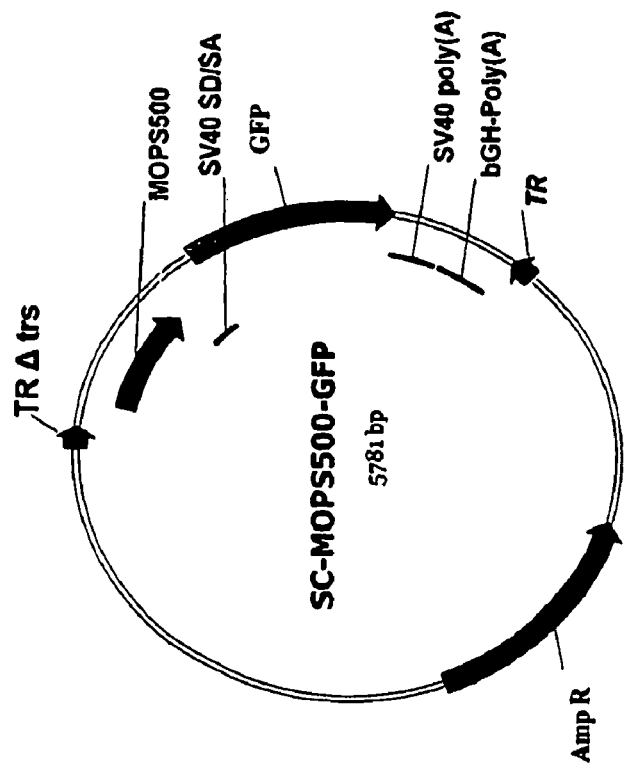
FIGS. 11A and 11B show self-complementary adeno-associated (scAAV) vector constructs of the invention.
Figure 11A:
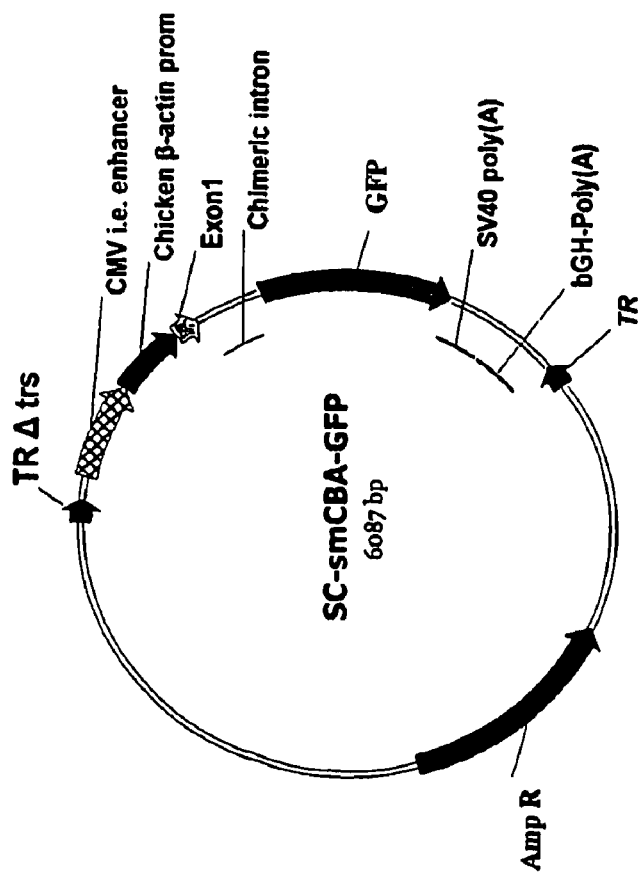
Figures 12A, 12B, 12C:
FIGS. 12A-12C show adult mouse retina after subretinal injection with scAAV5-smCBA-GFP. Sections stained with anti-GFP show intense RPE signal with less intense photoreceptor signal.
Figure 13:
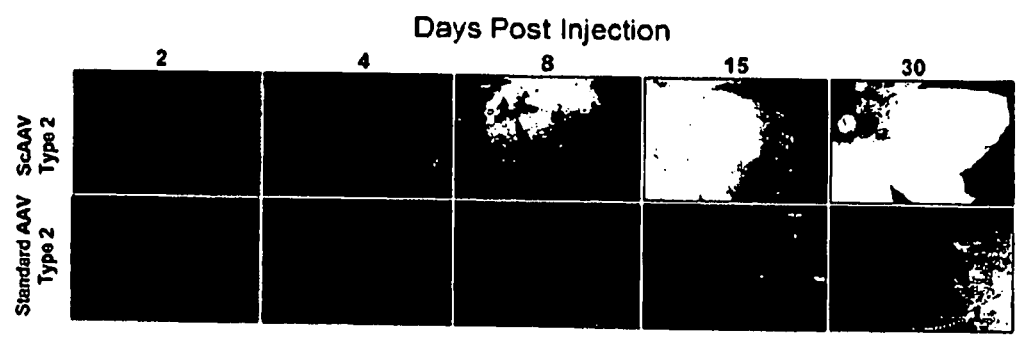
FIG. 13 shows whole mount mouse retina after subretinal injection of type 2 self complimentary AAV (scAAV) or type 2 standard AAV expressing green fluorescent protein under the control of smCBA.
Figure 14:
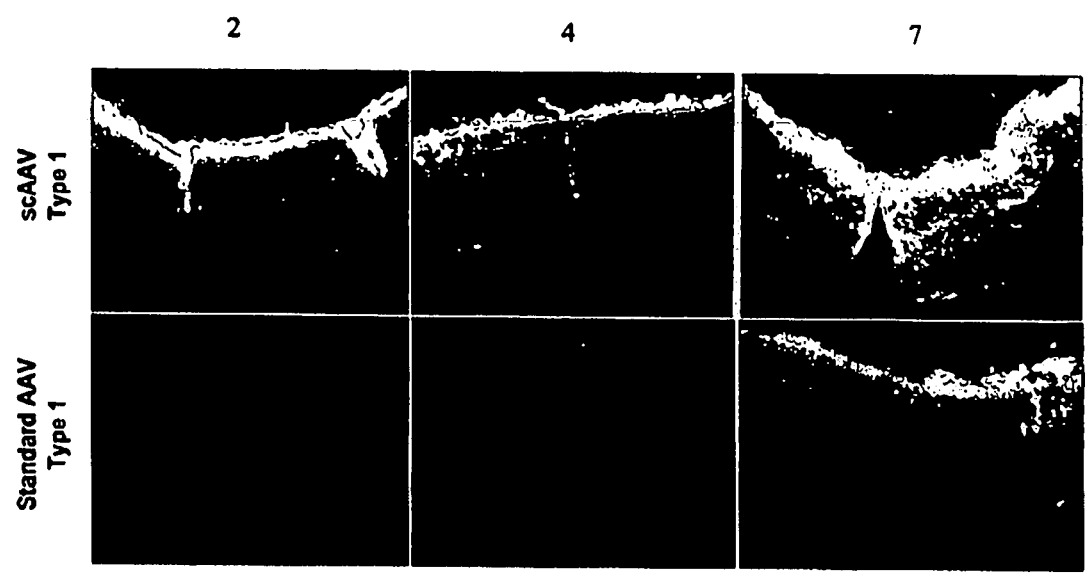
FIG. 14 shows adult mouse retina after subretinal injection with either scAAV1-smCBA or AAV1-CBA-GFP. Sections stained with anti-GFP and counterstained with DAPI. The RPE supports strong GFP expression with weaker photoreceptor expression also evident.
Figure 15:
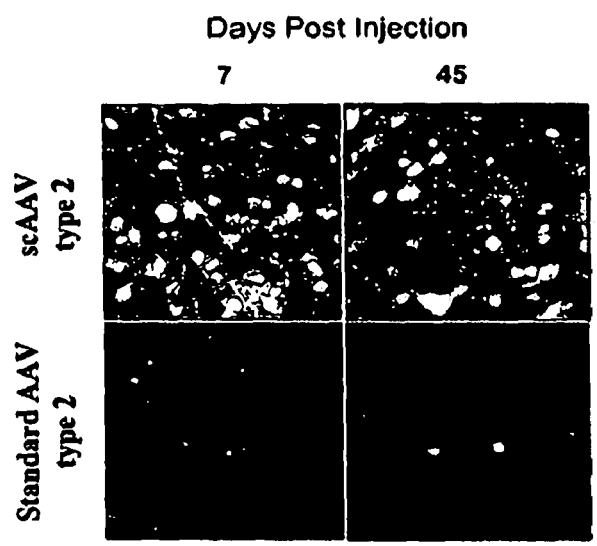
FIG. 15 shows whole mount adult mouse retina after intravitreal injection with scAAV2-smCBA-GFP. Staining with anti-GFP antibody shows rapid, intense ganglion cell signal. 40× magnification.
Figure 16:
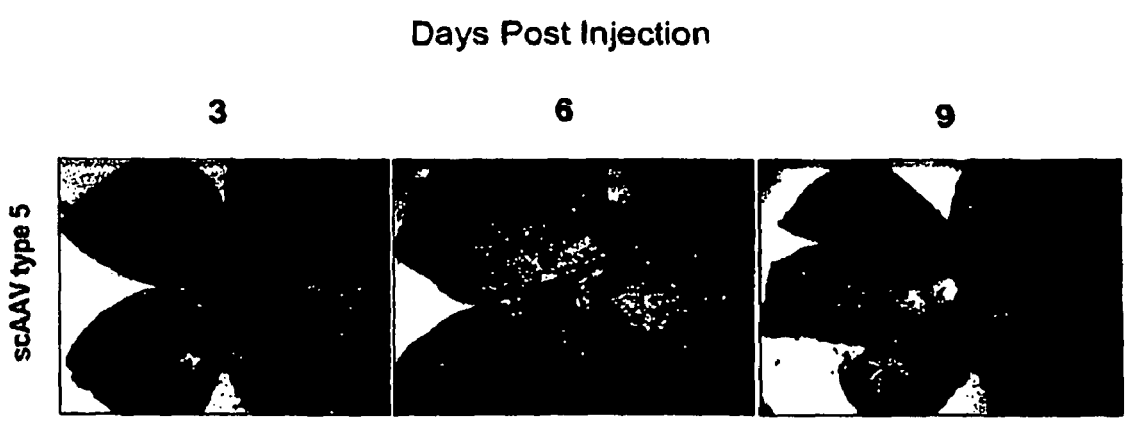
FIG. 16 shows whole mount adult mouse retina stained with anti-GFP after subretinal injection with scAAV5-MOPS-GFP.

AAV vectors with the mouse opsin promoter (MOPS) (Flannery et al., *Proc Natl Acad Sci USA*, 1997, 94(13):6916-21, which is incorporated herein by reference in its entirety) and an abbreviated version of the chimeric CMV-chicken β-actin promoter (smCBA) (described in Example 1) driving humanized green fluorescent protein (GFP) were already available in the inventors' laboratory. Matching scAAV vectors were made from vector plasmid with a mutation in one of the terminal resolution sequences of the AAV virus (McCarty et al., *Gene Ther.*, 2003, 10(26):2112-2118, which is incorporated herein by reference in its entirety) (shown in FIGS. 11A and 11B).

B. Comparison of scAAV to AAV Vectors in Mouse Retina

Subretinal or intravitreal injections of serotype 1, 2 and 5 scAAV and AAV vectors with matching promoters expressing green fluorescent protein (GFP) were performed in adult mice. In some cases, injections with matching standard AAV vectors were done for direct comparison. GFP expression was evaluated in retinal whole mounts and in sections by direct GFP fluorescence or GFP immunohistochemistry. Results are shown in FIGS. 12-16.

C. Conclusions

Self-complimentary AAV vectors support onset of strong passenger gene expression in RPE cells, retinal ganglion cells and photoreceptors within 2 days. The rapidity of expression onset is independent of the AAV vector serotype tested: 1, 2 and 5. In side-by-side experiments, self-complimentary AAV vector expresses passenger genes significantly more rapidly that conventional single-stranded AAV vectors, and at potentially higher levels.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

TABLE 1

Examples of Host Cells

Keratinizing Epithelial Cells
  keratinocyte of epidermis
  basal cell of epidermis
  keratinocyte of fingernails and toenails
  basal cell of nail bed
  hair shaft cells
    medullary
    cortical
    cuticular
  hair-root sheath cells
    cuticular
    of Huxley's layer
    of Henle's layer
    external
  hair matrix cell
Cells of Wet Stratified Barrier Epithelia
  surface epithelial cell of stratified squamous epithelium of cornea tongue, oral cavity, esophagus, anal canal, distal urethra, vagina
  basal cell of these epithelia
  cell of urinary epithelium
Epithelial Cells Specialized for Exocrine Secretion
  cells of salivary gland
    mucous cell
    serous cell
  cell of von Ebner's gland in tongue
  cell of mammary gland, secreting milk
  cell of lacrimal gland, secreting tears
  cell of ceruminous gland of ear, secreting wax
  cell of eccrine sweat gland, secreting glycoproteins
  cell of eccrine sweat gland, secreting small molecules
  cell of apocrine sweat gland
  cell of gland of Moll in eyelid
  cell of sebaceous gland, secreting lipid-rich sebum
  cell of Bowman's gland in nose
  cell of Brunner's gland in duodenum, secreting alkaline solution of mucus and enzymes
  cell of seminal vesicle, secreting components of seminal fluid, including fructose
  cell of prostate gland, secreting other components of seminal fluid
  cell of bulbourethral gland, secreting mucus
  cell of Bartholin's gland, secreting vaginal lubricant
  cell of gland of Littre, secreting mucus
  cell of endometrium of uterus, secreting mainly carbohydrates
  isolated goblet cell of respiratory and digestive tracts, secreting mucus
  mucous cell of lining of stomach
  zymogenic cell of gastric gland, secreting pepsinogen
  oxyntic cell of gastric gland, secreting HCl TABLE 1-continued Examples of Host Cells acinar cell of pancreas, secreting digestive enzymes and bicarbonate
Paneth cell of small intestine, secreting lysozyme
type II pneumocyte of lung, secreting surfactant
Clara cell of lung
Cells Specialized for Secretion of Hormones
cells of anterior pituitary, secreting
   growth hormone
   follicle-stimulating hormone
   luteinizing hormone
   prolactin
   adrenocorticotropic hormone
   thyroid-stimulating hormone
cell of intermediate pituitary, secreting melanocyte-stimulating hormone
cells of posterior pituitary, secreting
   oxytocin
   vasopressin
cells of gut and respiratory tract, secreting
   serotonin
   endorphin
   somatostatin
   gastrin
   secretin
   cholecystokinin
   insulin
   glucagons
   bombesin
cells of thyroid gland, secreting
   thyroid hormone
   calcitonin
cells of parathyroid gland, secreting
   parathyroid hormone
   oxyphil cell
cells of adrenal gland, secreting
   epinephrine
   norepinephrine
   steroid hormones
      mineralocorticoids
      glucocorticoids
cells of gonads, secreting
   testosterone
   estrogen
   progesterone
cells of juxtaglomerular apparatus of kidney
   juxtaglomerular cell
   macula densa cell
   peripolar cell
   mesangial cell
Epithelial Absorptive Cells in Gut, Exocrine Glands, and Urogenital Tract
brush border cell of intestine
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
Cells Specialized for Metabolism and Storage
hepatocyte
fat cells (e.g., adipocyte)
   white fat
   brown fat
   lipocyte of liver
Epithelial Cells Serving Primarily a Barrier Function, Lining the Lung, Gut, Exocrine Glands, and Urogenital Tract
type I pneumocyte
pancreatic duct cell
nonstriated duct cell of sweat gland, salivary gland, mammary gland, etc.
parietal cell of kidney glomerulus
podocyte of kidney glomerulus
cell of thin segment of loop of Henle
collecting duct cell
duct cell of seminal vesicle, prostate gland, etc.
Epithelial Cells Lining Closed Internal Body Cavities
vascular endothelial cells of blood vessels and lymphatics
(e.g., microvascular cell)
   fenestrated
   continuous
   splenic
synovial cell
serosal cell
squamous cell lining perilymphatic space of ear
cells lining endolymphatic space of ear
   squamous cell
   columnar cells of endolymphatic sac
      with microvilli
      without microvilli
   "dark" cell
   vestibular membrane cell
   stria vascularis basal cell
   stria vascularis marginal cell
   cell of Claudius
   cell of Boettcher
choroid plexus cell
squamous cell of pia-arachnoid
cells of ciliary epithelium of eye
   pigmented
   nonpigmented
corneal "endothelial" cell
Ciliated Cells with Propulsive Function
of respiratory tract
of oviduct and of endometrium of uterus
of rete testis and ductulus efferens
of central nervous system
Cells Specialized for Secretion of Extracellular Matrix
epithelial:
   ameloblast
   planum semilunatum cell of vestibular apparatus of ear
   interdental cell of organ of Corti
nonepithelial:
   fibroblasts
   pericyte of blood capillary (Rouget cell)
   nucleus pulposus cell of intervertebral disc
   cementoblast/cementocyte
   odontoblast/odontocyte
   chondrocytes
      of hyaline cartilage
      of fibrocartilage
      of elastic cartilage
   osteoblast/osteocyte
   osteoprogenitor cell
   hyalocyte of vitreous body of eye
   stellate cell of perilymphatic space of ear
Contractile Cells
skeletal muscle cells
   red
   white
   intermediate
   muscle spindle-nuclear bag
   muscle spindle-nuclear chain
   satellite cell
heart muscle cells
   ordinary
   nodal
   Purkinje fiber
   Cardiac valve tissue
smooth muscle cells
myoepithelial cells:
   of iris
   of exocrine glands
Cells of Blood and Immune System
red blood cell (erythrocyte)
megakaryocyte
macrophages
   monocyte
   connective tissue macrophage
   Langerhan's cell
   osteoclast
   dendritic cell
   microglial cell
neutrophil
eosinophil
basophil
mast cell
plasma cell
T lymphocyte
   helper T cell TABLE 1-continued Examples of Host Cells suppressor T cell
killer T cell
B lymphocyte
  IgM
  IgG
  IgA
  IgE
killer cell
stem cells and committed progenitors for the blood and immune system
Sensory Transducers
photoreceptors
  rod
  cones
    blue sensitive
    green sensitive
    red sensitive
hearing
  inner hair cell of organ of Corti
  outer hair cell of organ of Corti
acceleration and gravity
  type I hair cell of vestibular apparatus of ear
  type II hair cell of vestibular apparatus of ear
taste
  type II taste bud cell
smell
  olfactory neuron
  basal cell of olfactory epithelium
blood pH
  carotid body cell
    type I
    type II
touch
  Merkel cell of epidermis
  primary sensory neurons specialized for touch
temperature
  primary sensory neurons specialized for temperature
    cold sensitive
    heat sensitive
pain
  primary sensory neurons specialized for pain
configurations and forces in musculoskeletal system
  proprioceptive primary sensory neurons TABLE 1-continued Examples of Host Cells Autonomic Neurons
  cholinergic
  adrenergic
  peptidergic
Supporting Cells of Sense Organs and of Peripheral Neurons
  supporting cells of organ of Corti
    inner pillar cell
    outer pillar cell
    inner phalangeal cell
    outer phalangeal cell
    border cell
    Hensen cell
  supporting cell of vestibular apparatus
  supporting cell of taste bud
  supporting cell of olfactory epithelium
  Schwann cell
  satellite cell
  enteric glial cell
Neurons and Glial Cells of Central Nervous System
  neurons
  glial cells
    astrocyte
    oligodendrocyte
Lens Cells
  anterior lens epithelial cell
  lens fiber
Pigment Cells
  melanocyte
  retinal pigmented epithelial cell
  iris pigment epithelial cell
Germ Cells
  oogonium/oocyte
  spermatocyte
  Spermatogonium
  blast cells
  fertilized ovum
Nurse Cells
  ovarian follicle cell
  Sertoli cell
  thymus epithelial cell (e.g., reticular cell)
  placental cell

We claim:

1. A vector comprising a truncated chimeric CMV-chicken β-actin promoter, wherein the vector is a self-complementary adeno-associated virus (scAAV), and wherein said truncated chimeric CMV-chicken β-actin promoter consists of the nucleic acid sequence of SEQ ID NO:1.

2. The vector of claim 1, further comprising a heterologous polynucleotide operably linked to the truncated chimeric CMV-chicken β-actin promoter.

3. The vector of claim 2, wherein the heterologous polynucleotide encodes a polypeptide, an interfering RNA molecule or an antisense oligonucleotide.

4. The vector of claim 1, wherein the vector further comprises a polynucleotide encoding a detectable reporter polypeptide.

5. The vector of claim 4, wherein the detectable reporter polypeptide is beta-globin, luciferase, beta-galactosidase, or a fluorescent protein.

6. The vector of claim 5, wherein the fluorescent protein is a green fluorescent protein (GFP).

7. A method of delivering a vector to an isolated cell comprising: administering the vector of claim 2 to an isolated cell such that the heterologous polynucleotide is expressed in the cell.

8. The method of claim 7, wherein the isolated cell is a human or non-human animal cell.

9. The method of claim 7, wherein the isolated cell is a brain, liver, lung, cardiac, ocular or smooth muscle cell.

10. The method of claim 7, wherein the isolated cell is a neuron.

11. The method of claim 7, wherein the polynucleotide encodes a polypeptide, an interfering RNA molecule or an antisense oligonucleotide.

* * * * *

UNITED STATES PATENT AND TRADEMARK OFFICE
CERTIFICATE OF CORRECTION

PATENT NO. : 8,298,818 B2
APPLICATION NO. : 12/298845
DATED : October 30, 2012
INVENTOR(S) : Sanford Leon Boye, Barry John Byrne and William W. Hauswirth It is certified that error appears in the above-identified patent and that said Letters Patent is hereby corrected as shown below:

Column 2
Line 45, "phosphodiesterase β-PDE)" should read --phosphodiesterase (β-PDE)--

Column 6
Line 47, "wild-type normal)" should read --wild-type (*i.e.*, normal)--

Column 7
Line 4, "145 by" should read --145 bp--

Line 5, "125 by" should read --125 bp--

Line 36, "Similarly; the" should read --Similarly, the--

Column 17
Line 61, "plurality, of cells" should read --plurality of cells--

Column 19
Line 14, "in the Gel" should read --in the GC1--

Signed and Sealed this
Fifth Day of February, 2013

Teresa Stanek Rea
*Acting Director of the United States Patent and Trademark Office*